United States Patent
Tange

(10) Patent No.: US 9,137,186 B2
(45) Date of Patent: Sep. 15, 2015

(54) APPARATUS, METHOD, AND PROGRAM FOR EXCHANGING MESSAGE OR MAKING VOICE CALL VIA NETWORK

(75) Inventor: Masaru Tange, Tokyo (JP)

(73) Assignee: SCENTEE HOLDINGS PTE LTD., Tokyo (JP)

( * ) Notice: Subject to any disclaimer, the term of this patent is extended or adjusted under 35 U.S.C. 154(b) by 0 days.

(21) Appl. No.: 14/127,686

(22) PCT Filed: May 31, 2012

(86) PCT No.: PCT/JP2012/064022
§ 371 (c)(1),
(2), (4) Date: Dec. 19, 2013

(87) PCT Pub. No.: WO2013/001972
PCT Pub. Date: Jan. 3, 2013

(65) Prior Publication Data
US 2014/0189026 A1 Jul. 3, 2014

(30) Foreign Application Priority Data

Jun. 30, 2011 (JP) .................................. 2011-146899

(51) Int. Cl.
*G06F 15/16* (2006.01)
*H04L 12/58* (2006.01)
(Continued)

(52) U.S. Cl.
CPC .................. *H04L 51/10* (2013.01); *A61L 9/125* (2013.01); *A61L 9/14* (2013.01); *H04M 1/21* (2013.01); *A61L 2209/11* (2013.01); *A61L 2209/133* (2013.01); *H04M 1/72547* (2013.01)

(58) Field of Classification Search
CPC ......... H04L 51/10; H04L 67/04; H04L 67/20; H04W 4/001; H04W 4/023
See application file for complete search history.

(56) References Cited

U.S. PATENT DOCUMENTS

| 8,472,976 | B1 * | 6/2013 | Ledet | ......................... 455/456.1 |
| 2004/0204043 | A1 | 10/2004 | Wang et al. | |
| 2007/0258849 | A1 * | 11/2007 | Kent | ................................ 422/5 |

FOREIGN PATENT DOCUMENTS

| EP | 1598084 A1 | 11/2005 |
| JP | 2002-77444 A1 | 3/2002 |

(Continued)

OTHER PUBLICATIONS

European Office Action dated Oct. 9, 2014.
(Continued)

*Primary Examiner* — Djenane Bayard
(74) *Attorney, Agent, or Firm* — Kratz, Quintos & Hanson, LLP

(57) ABSTRACT

[Object] To provide a means that enables information exchange with more fun by reducing dull and uninteresting impression in the information exchanged via a network.
[Solution] Each member of an instant messaging system 1 connects an aroma emitting adapter 13 to a terminal device 12 and loads an aroma cartridge 14 containing aroma liquid in the aroma emitting adapter 13, whereby the member can log on a messaging server device 11. The terminal device 12 of the member who logs onto displays names of the members with whom the message exchange or conversation can be made among the other members who are currently logged on. Upon the reception of the message or voice calling from another member, the terminal device 12 instructs the aroma emitting adapter 13 to emit the aroma and the aroma emitting adapter 13 thus emits aroma by releasing the aroma liquid contained in the aroma cartridge 14. As a result, the message or conversation can be accompanied by the aroma.

26 Claims, 14 Drawing Sheets

(51) Int. Cl.
*H04M 1/21* (2006.01)
*A61L 9/12* (2006.01)
*A61L 9/14* (2006.01)
*H04M 1/725* (2006.01)

(56) References Cited

FOREIGN PATENT DOCUMENTS

| | | | |
|---|---|---|---|
| JP | 2003-283631 | A1 | 10/2003 |
| JP | 2003-325650 | A1 | 11/2003 |
| JP | 2004-159908 | A1 | 6/2004 |
| JP | 2005-295414 | A1 | 10/2005 |
| JP | 2006-140694 | A1 | 6/2006 |
| WO | 2010058382 | A1 | 5/2010 |

OTHER PUBLICATIONS

International Search Report for International Application No. PCT/JP2012/064022 dated Jul. 31, 2012.

* cited by examiner

Fig. 4
(a)
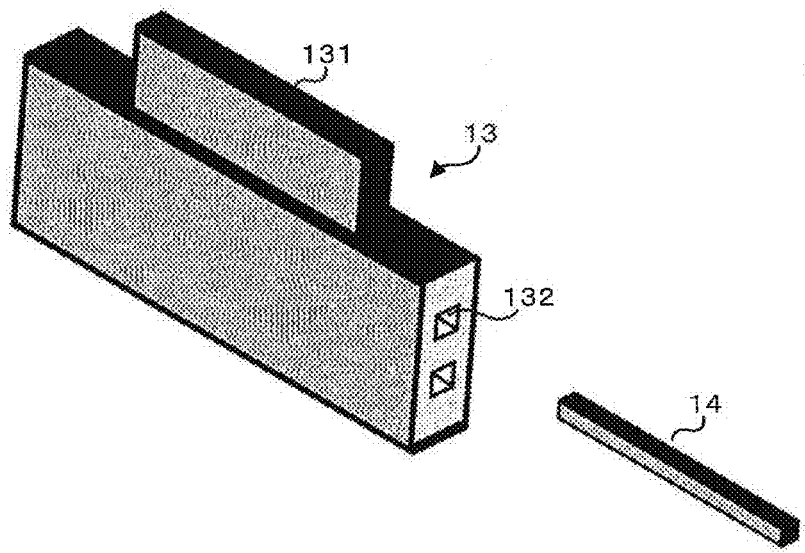
(b)
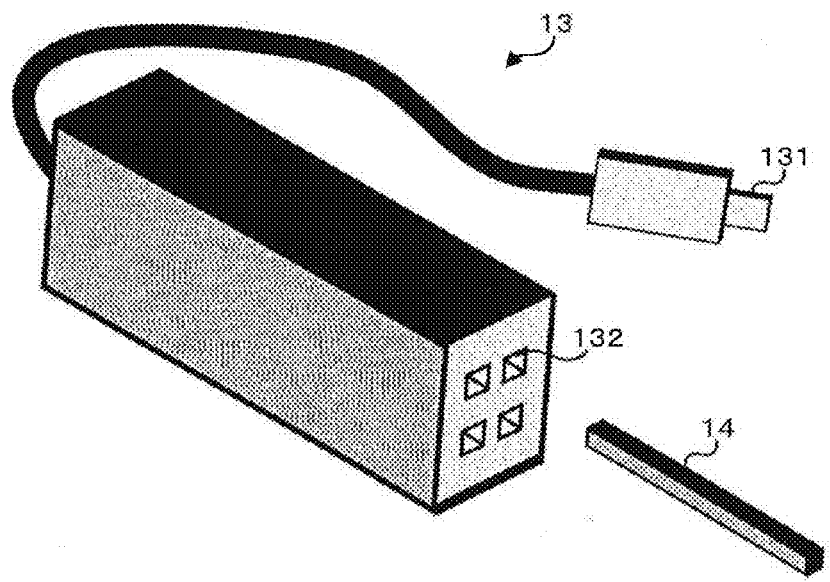

Fig. 6
(a)
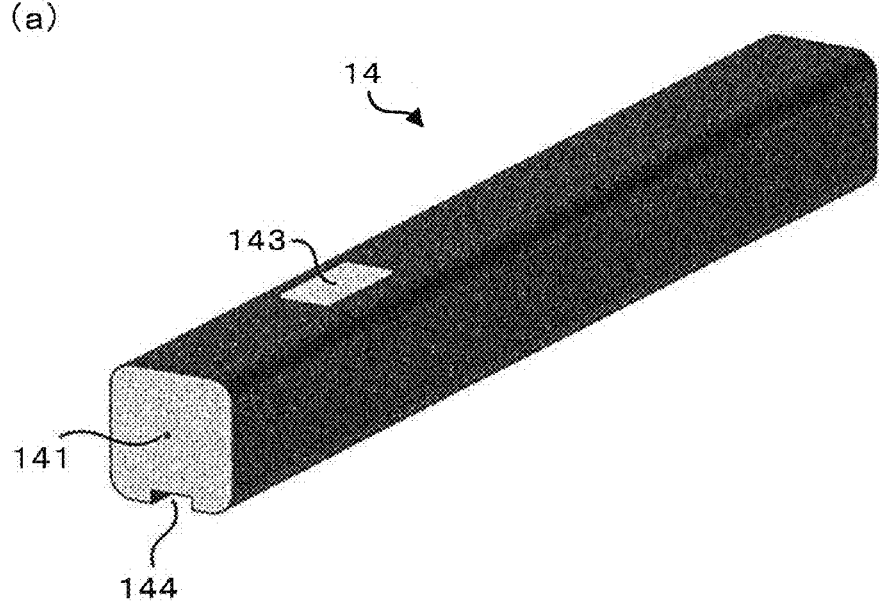
(b)
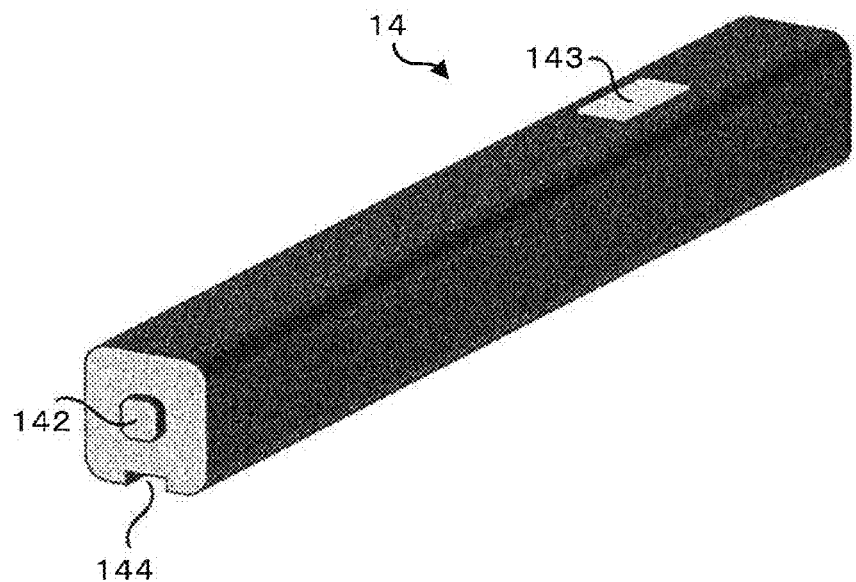

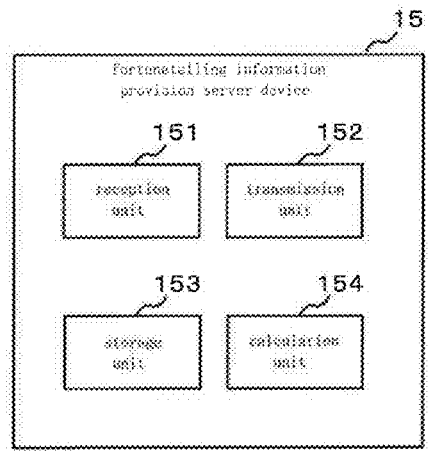

Fig. 9

| Cartridge type ID | Cartridge name data | Aroma base name data | Access condition data | Aroma explanation data |
|---|---|---|---|---|
| ... | ... | ... | ... | ... |
| ... | ... | ... | ... | ... |
| ... | ... | ... | ... | ... |

Fig. 10

| User ID | Password | Email address |
|---|---|---|
| ... | ... | ... |
| ... | ... | ... |
| ... | ... | ... |

APPARATUS, METHOD, AND PROGRAM FOR EXCHANGING MESSAGE OR MAKING VOICE CALL VIA NETWORK

TECHNICAL FIELD

The present invention relates to a technique for exchanging messages or making a voice call among a number of members via a network.

BACKGROUND ART

Systems for exchanging text messages or making a voice call via a public communication network such as the Internet or mobile communication network have become popular.

For example, in a system generally referred to as an instant messaging system, once a member logs onto a predetermined server device through a terminal device, he/she can exchange messages or make a voice call in real time with another member who is currently logged onto the system among the members whom he/she has allowed to exchange the message with.

Some of such instant messaging systems even enable a video call that uses not just voice but also video or enable the exchange of data files.

For example, Patent Document 1 discloses a system as follows: when, while a member exchanges text messages with another member, a third member makes a call to the member and a conversation is started, the anxiety or the discomfort of the member with whom the text messages have been exchanged can be relieved by sending notification to the member that the message cannot be replied because the member is now on a call.

CITATION LIST

Patent Document

Patent Document 1: Japanese Unexamined Patent Application Publication No. 2005-295414

SUMMARY OF INVENTION

Technical Problem

With a conventional instant messaging system, members far away from each other can exchange various information using text, voice, or images. Those messages, however, give somewhat dull and uninteresting impression as compared with the messages exchanged face-to-face in reality.

In view of the above circumstances, an object of the present invention is to provide a means that reduces the dull and uninteresting impression in the information exchange via the network and enables the information exchange with more fun.

Solution to problem

Among the five senses of humans, it is said that the sense of smell is more primitive and affects the instinct stronger than the other senses. In recent years, the effects from aroma, for example, aroma that people feel comfortable with can relax human body and eliminate exhaustion have come to be widely known, and thus the service called aromatherapy has become popular these days.

The inventor of the present application has conceived that the conventional information exchange via the network with the dull and uninteresting impression can be changed into information exchange with more fun by utilizing the aroma having such effects. Specific description is made below.

A first aspect of the present invention is a server device including a reception means that receives data transmitted from another communication device;

a storage means that stores the data;

a calculation means that performs a calculation process; and a transmission means that transmits the data to another communication device, wherein:

the reception means receives from any of a plurality of terminal devices capable of having an aroma cartridge as a cartridge containing aroma liquid loaded therein, terminal identification data for identifying the terminal device and cartridge identification data for identifying the aroma cartridge currently loaded or a type of aroma liquid contained in the aroma cartridge;

the storage means stores, while associating with the terminal identification data received from one terminal device by the reception means, the cartridge identification data received from the one terminal device as the entire or a part of attribute data representing an attribute of the one terminal device;

the reception means receives from any terminal device of the plural terminal devices, request data for requesting transmission of status data representing the current loading state of the aroma cartridge in each of one or more terminal devices among the plural terminal devices;

the calculation means generates, upon the reception of the request data in the reception unit, the status data based on the terminal identification data stored in the storage means and the attribute data stored while being associated with the terminal identification data in response to the request data; and the transmission means transmits the status data generated by the calculation means to the terminal device that has transmitted the request data.

A second aspect of the present invention is a preferred embodiment of the server device according to the above first aspect, wherein:

the reception means receives from any terminal device of the plural terminal devices, message data representing a message or voice calling data representing a calling addressed to a terminal device that is different from the any terminal device of the plural terminal devices; and the transmission means transmits the message data or the voice calling data to the terminal device to which the message data or the voice calling data are addressed, upon the reception of the message data or the voice calling data in the reception means.

A third aspect of the present invention is a preferred embodiment of the server device according to the second aspect, wherein:

the storage means stores judging condition data representing a condition for judging whether exchange of message data representing a message or voice calling data representing a calling among the plural terminal devices is allowed or not based on the terminal identification data stored in the storage means or the attribute data stored while being associated with the terminal identification data; and the calculation means judges the terminal device to which the message data or the voice calling data can be transmitted on the basis of the judging condition data stored in the storage means and generates the status data related to the judged terminal device.

A fourth aspect of the present invention is a preferred embodiment of the server device according to any of the above first to third aspects, wherein:

the reception means receives from any terminal device of the plural terminal devices, at least one of data on the number of times of releases representing the number of times of releasing the aroma liquid from the aroma cartridge loaded in the terminal device, data on the amount of release representing the amount of aroma liquid released from the aroma cartridge, and data on the remaining amount representing the remaining amount of the aroma liquid contained in the aroma cartridge; and the storage means stores at least one of the data on the number of times of releases, the data on the amount of release, and the data on the remaining amount that has been received by the reception means, as a part of the attribute data, while associating the data with the terminal identification data for identifying the terminal device that has transmitted the data.

A fifth aspect of the present invention is a preferred embodiment of the server device according to any of the above first to fourth aspects, wherein:

the reception means receives from any terminal device of the plural terminal devices, positional data representing current location of the terminal device;

the storage means stores the positional data received by the reception means as a part of the attribute data while associating the positional data with the terminal identification data for identifying the terminal device that has transmitted the positional data; and the calculation means generates the status data representing the position of each terminal device on a map on the basis of the positional data included in the attribute data stored in the storage means.

A sixth aspect of the present invention is a preferred embodiment of the server device according to any of the first to fifth aspects, wherein:

the reception means receives from a communication device, extraction condition data representing a condition for extracting one or more terminal devices on the basis of the terminal identification data or the attribute data;

the calculation means extracts the terminal identification data satisfying the condition represented by the extraction condition data received by the reception means and the attribute data stored while being associated with the terminal identification data, from among the terminal identification data stored in the storage means and the attribute data stored while being associated with the terminal identification data; and the transmission means transmits to the communication device, the terminal identification data and the attribute data stored while being associated with the terminal identification data that have been extracted by the calculation means.

A seventh aspect of the present invention is a preferred embodiment of the server device according to any of the first to sixth aspects, wherein:

the reception means receives the extraction condition data representing the condition for extracting one or more terminal devices on the basis of the attribute data from any terminal device of the plural terminal devices; and the calculation means extracts the attribute data satisfying the condition represented by the extraction condition data received by the reception means from the terminal device from among the attribute data stored in the storage means, and generates the status data related to the terminal device represented by the terminal identification data stored in the storage means while being associated with the extracted attribute data.

An eighth aspect of the present invention is a method including:

a step in which a server device receives from any terminal device of a plural terminal devices to which an aroma cartridge as a cartridge containing aroma liquid can be loaded, terminal identification data for identifying the terminal device and cartridge identification data for identifying the aroma cartridge currently loaded or a type of aroma liquid contained in the aroma cartridge;

a step in which the server device stores, while associating with the terminal identification data received from one terminal device, the cartridge identification data received from the one terminal device as the entire or apart of attribute data representing an attribute of the one terminal device;

a step in which the server device receives from any terminal device of the plural terminal devices, request data for requesting transmission of status data representing the current loading state of the aroma cartridge in each of one or more terminal devices among the plural terminal devices;

a step in which the server device generates, upon the reception of the request data, the status data based on the stored terminal identification data and the attribute data stored while being associated with the terminal identification data in response to the request data; and a step in which the server device transmits the generated status data to the terminal device that has transmitted the request data.

A ninth aspect of the present invention is a preferred embodiment of the method according to the eighth aspect, further including:

a step in which the server device receives from any terminal device of the plural terminal devices, message data representing a message or voice calling data representing a calling addressed to a terminal device that is different from the any terminal device of the plural terminal devices; and a step in which the server device transmits the message data or the voice calling data to the terminal device to which the message data or the voice calling data are addressed, upon the reception of the message data or the voice calling data.

A tenth aspect of the present invention is a preferred embodiment of the method according to the ninth aspect, further including a step in which the server device stores judging condition data representing a condition for judging whether exchange of message data representing a message or voice calling data representing a calling among the plural terminal devices is allowed or not based on the stored terminal identification data or the attribute data stored while being associated with the terminal identification data, wherein in the step of generating the status data, the server device judges the terminal device to which the message data or the voice calling data can be transmitted on the basis of the stored judging condition data and generates the status data related to the judged terminal device.

An eleventh aspect of the present invention is a preferred embodiment of the method according to any of the eighth to tenth aspects, further including:

a step in which the server device receives from any terminal device of the plural terminal devices, at least one of data on the number of times of releases representing the number of times of releasing the aroma liquid from the aroma cartridge loaded in the terminal device, data on the amount of release representing the amount of aroma liquid released from the aroma cartridge, and data on the remaining amount representing the remaining amount of the aroma liquid contained in the aroma cartridge; and a step in which the server device stores at least one of the data on the number of times of releases, the data on the amount of release, and the data on the remaining amount that has been received, as a part of the attribute data, while associating the data with the terminal identification data for identifying the terminal device that has transmitted the data.

A twelfth aspect of the present invention is a preferred embodiment of the method according to any of the eighth to the eleventh aspects, further including:

a step in which the server device receives from any terminal device of the plural terminal devices, positional data representing current location of the terminal device; and a step in which the server device stores the received positional data as a part of the attribute data while associating the positional data with the terminal identification data for identifying the terminal device that has transmitted the positional data, wherein in the step of generating the status data, the server device generates the status data representing the position of each terminal device on a map on the basis of the positional data included in the stored attribute data.

A thirteenth aspect of the present invention is a preferred embodiment of the method according to any of the eighth to twelfth aspects, further including:

a step in which the server device receives from a communication device, extraction condition data representing a condition for extracting one or more terminal devices on the basis of the terminal identification data or the attribute data;

a step in which the server device extracts the terminal identification data satisfying the condition represented by the received extraction condition data and the attribute data stored while being associated with the terminal identification data, from among the stored terminal identification data and the attribute data stored while being associated with the terminal identification data; and a step in which the server device transmits to the communication device, the terminal identification data and the attribute data stored while being associated with the terminal identification data that have been extracted.

A fourteenth aspect of the present invention is a preferred embodiment of the method according to any of the eighth to thirteenth aspects, further including a step in which the server device receives the extraction condition data representing the condition for extracting one or more terminal devices on the basis of the attribute data from any terminal device of the plural terminal devices, wherein in the step of generating the status data, the server device extracts the attribute data satisfying the condition represented by the extraction condition data received from the terminal device from among the stored attribute data, and generates the status data related to the terminal device represented by the terminal identification data stored while being associated with the extracted attribute data.

A fifteenth aspect of the present invention is a program allowing a computer having a communication means that performs data communication with another communication device to function as the reception means, the storage means, the calculation means, and the transmission means included in the server device according to any of the first to seventh aspects described above.

A sixteenth aspect of the present invention is a terminal device including:

a reception means that receives data transmitted from another communication device;

a storage means that stores the data;

a transmission means that transmits the data to another communication device;

a display means that displays an image;

an input means that accepts data input from a user by generating predetermined data in response to predetermined user operation; an aroma generating means that generates aroma; and a control means that controls another configuration part, wherein:

the aroma generating means includes a hollow part that accepts loading of an aroma cartridge as a cartridge containing aroma liquid, a release means that releases a part of the aroma liquid contained in the aroma cartridge loaded in the hollow part, and a reading means that reads data recorded in the aroma cartridge loaded in the hollow part;

the transmission means transmits to a server device, terminal identification data for identifying the own device stored in the storage means or terminal identification data for identifying the own device generated by the input means in response to user operation;

the reading means reads the data recorded in the aroma cartridge currently loaded in the hollow part;

the transmission means transmits to the server device, cartridge identification data for identifying the aroma cartridge or a type of the aroma liquid included in the data read by the reading means;

the transmission means transmits to the server device, request data for requesting transmission of status data representing the current loading state of the aroma cartridge in each of one or more terminal devices among the plural terminal devices except the own device;

the reception means receives the status data transmitted from the server device as a response to the request data transmitted by the transmission means; and the display means displays an image representing content of the status data received by the reception means.

A seventeenth aspect of the present invention is a preferred embodiment of the terminal device according to the sixteenth aspect, wherein:

the reception means receives from the server device, message data representing a message or voice calling data representing a calling from a terminal device that is different from the own terminal device; and the control means causes the release means to release the aroma liquid upon the reception of the message data or the voice calling data in the reception unit.

An eighteenth aspect of the present invention is a preferred embodiment of the terminal device according to any of the sixteenth or seventeenth aspect, wherein the transmission means transmits to the server device, at least one of data on the number of times of releases representing the number of times of releasing the aroma liquid from the aroma cartridge loaded in the hollow part, data on the amount of release representing the amount of aroma liquid released from the aroma cartridge, and data on the remaining amount representing the remaining amount of the aroma liquid contained in the aroma cartridge.

A nineteenth aspect of the present invention is a preferred embodiment of the terminal device according to any of the sixteenth to eighteenth aspects, further including a positional data acquiring means that acquires positional data representing a current position of the own device, wherein the transmission means transmits the positional data acquired by the positional data acquiring means to the server device.

A twentieth aspect of the present invention is a preferred embodiment of the terminal device according to any of the sixteenth to nineteenth aspects, wherein:

the input means generates extraction condition data representing a condition for extracting one or more terminal devices on the basis of attribute data representing an attribute of the terminal device in response to user operation;

the transmission means transmits the extraction condition data generated by the input means to the server device; and the reception means receives the status data related to the terminal device extracted in the server device on the basis of the extraction condition data transmitted from the transmission means.

A twenty-first aspect of the present invention is a method including:

a step in which a terminal device including an aroma generating means for generating aroma transmits to a server device, terminal identification data for identifying the stored own device or terminal identification data for identifying the own device generated in response to user operation;

a step in which the terminal device reads data recorded in an aroma cartridge as a cartridge containing aroma liquid loaded in the aroma generating means;

a step in which the terminal device transmits to the server device, cartridge identification data for identifying the aroma cartridge or a type of the aroma liquid included in the read data;

a step in which the terminal device transmits to the server device, request data for requesting transmission of status data representing a current loading state of the aroma cartridge in each of one or more terminal devices of plural terminal devices except the own device;

a step in which the terminal device receives the status data transmitted from the server device as a response to the transmitted request data; and a step in which the terminal device displays an image representing content of the received status data.

A twenty-second aspect of the present invention is a preferred embodiment of the method according to the twenty-first aspect, further including:

a step in which the terminal device receives from the server device, message data representing a message or voice calling data representing a calling transmitted from one terminal device of the plural terminal devices except the own device; and a step in which the terminal device causes the aroma generating means to release the aroma liquid from the aroma cartridge loaded in the aroma generating means upon the reception of the message data or the voice calling data.

A twenty-third aspect of the present invention is a preferred embodiment of the method according to the twenty-first or twenty-second aspect, further including a step in which the terminal device transmits to the server device, at least one of data on the number of times of releases representing the number of times of releasing the aroma liquid from the aroma cartridge loaded in the aroma generating means, data on the amount of release representing the amount of aroma liquid released from the aroma cartridge, and data on the remaining amount representing the remaining amount of the aroma liquid contained in the aroma cartridge.

A twenty-fourth aspect of the present invention is a preferred embodiment of the method according to any of the twenty-first to twenty-third aspects, further including:

a step in which the terminal device acquires positional data representing a current position of the own device; and a step in which the terminal device transmits the acquired positional data to the server device.

A twenty-fifth aspect of the present invention is a preferred embodiment of the method according to any of the twenty-first to twenty-fourth aspects, further including:

a step in which the terminal device generates extraction condition data representing a condition for extracting one or more terminal devices on the basis of attribute data representing an attribute of the terminal device in response to user operation; and a step in which the terminal device transmits the generated extraction condition data to the server device, wherein in the step of receiving the status data, the terminal device receives the status data related to the terminal device extracted in the server device on the basis of the transmitted extraction condition data.

A twenty-sixth aspect of the present invention is a program allowing a computer having a communication means that performs data communication with another communication device and an aroma generating means that generates aroma to function as the reception means, the storage means, the transmission means, the display means, the input means, and the control means included in the terminal device according to any of the sixteenth to twentieth aspects described above.

Advantageous Effects of Invention

With the server device according to the first aspect, the method according to the eighth aspect, the terminal device according to the sixteenth aspect, and the method according to the twenty-first aspect describe above, each member can know the information on the type of the aroma cartridge currently loaded in the terminal device of other members.

With the server device according to the second aspect, the method according to the ninth aspect, the terminal device according to the seventeenth aspect, and the method according to the twenty-second aspect, each member can cause the terminal device of another member having the terminal device with the aroma cartridge loaded therein to release the aroma liquid by transmitting a message or making a call, so that, for example, the member can present an aroma as a gift to make a friend working late at night feel relaxed.

With the server device according to the third aspect and the method according to the tenth aspect, a certain member can know the information on the type of the aroma cartridge currently loaded in the terminal device of only the members with whom the member has allowed to exchange the message or to have conversation. Therefore, each member can easily know to whom he/she can present the aroma as a gift.

With the server device according to the fourth aspect, the method according to the eleventh aspect, the terminal device according to the eighteenth aspect, and the method according to the twenty-third aspect, the information such as the type of the aroma liquid, the number of times of and the amount of releases of the aroma liquid in the past, and the remaining amount of the aroma liquid in the aroma cartridge currently loaded in the terminal device of each member can be used. Therefore, for example, the information such as the currently popular types of aromas can be provided in the form of ranking. Moreover, the provision of the additional information becomes possible; for example, for the members having not much aroma liquid left, the purchase of a new aroma cartridge is suggested based on the type of the aroma liquid used by the member in the past.

With the server device according to the fifth aspect, the method according to the twelfth aspect, the terminal device according to the nineteenth aspect, and the method according to the twenty-fourth aspect, each member can know the current location of other members along with the information on the type of the aroma cartridge currently loaded in the terminal device of those members, etc.

With the server device according to the sixth aspect and the method according to the thirteenth aspect, the server device for providing the additional information such as fortunetelling information can provide the fortunetelling information on the basis of the type of the aroma cartridge loaded currently or in the past in the terminal device of each member.

With the server device according to the seventh aspect, the method according to the fourteenth aspect, the terminal device according to the twentieth aspect, and the method according to the twenty-fifth aspect, each member can easily find out other members who have the aroma cartridge containing the similar aroma in the terminal device.

With the program according to the fifteenth aspect, the server device according to any of the first to seventh aspects can be realized using a computer. Similarly, with the program according to the twenty-sixth aspect, the terminal device according to any of sixteenth to twentieth aspects can be realized using a computer.

BRIEF DESCRIPTION OF DRAWINGS

FIG. 4 is an external view of an aroma emitting adapter according to an embodiment of the present invention.

FIG. 6 is an external view of an aroma cartridge according to an embodiment of the present invention.

FIG. 7 is a block diagram depicting the outline of the function configuration of a fortunetelling information provision server device according to an embodiment of the present invention.

FIG. 8 depicts an example of a data configuration of a user database stored in a messaging server device according to an embodiment of the present invention.

FIG. 9 depicts an example of a data configuration of a cartridge database stored in the messaging server device according to an embodiment of the present invention.

FIG. 10 depicts an example of a data configuration of a user database stored in the fortunetelling information provision server device according to an embodiment of the present invention.

DESCRIPTION OF EMBODIMENTS

1. Embodiment

The configuration and the operation of an instant messaging system 1 according to an embodiment of the present invention are described. Generally, the instant messaging system 1 is obtained by adding, to a conventional instant messaging system enabling the exchange of the text message or calling among the members who log onto the system, a function of emitting aroma from the terminal device of each member. In other words, in this instant messaging system 1, aroma liquid can be emitted at any timing from the terminal device of a friend or a stranger at a remote place. Further, in the instant messaging system 1, for example, various kinds of additional information on the aroma, such as the popular aroma and today's lucky aroma, can be provided.

1. 1. Configuration

Figure 1:
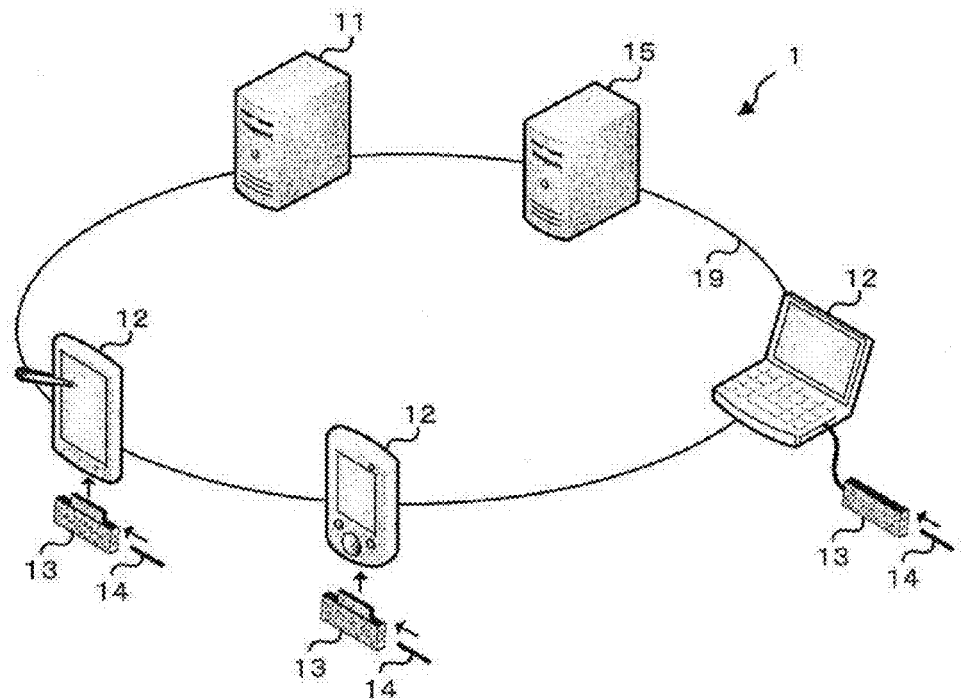
FIG. 1 is a block diagram depicting the entire configuration of an instant messaging system according to an embodiment of the present invention.

FIG. 1 is a block diagram of the entire structure of the instant messaging system 1. The instant messaging system 1 includes: a messaging server device 11 configured to manage various data along with the message and calling and transfer data between terminal devices, etc.; terminal devices 12 used by members of the instant messaging system 1 for exchanging messages; aroma emitting adapters 13 connected to the terminal devices 12 directly or via a cable and emitting aroma liquid; aroma cartridges 14 containing the aroma liquid and loaded in the aroma adapters 13; and a fortunetelling information provision server device 15 providing fortunetelling information to the members of the instant messaging system 1.

The terminal device 12 exchanges various data with the messaging server device 11 and the fortunetelling provision server device 15 via the Internet 19. The messaging server device 11 and the fortunetelling provision server device 15 also exchange various data via the Internet 19.

Although FIG. 1 depicts three sets of the terminal devices 12, the aroma emitting adapters 13 connected to the terminal devices 12, and the aroma cartridges 14 loaded in the aroma adapters 13, the number thereof is changeable depending on the number of members using the instant messaging system 1. Note that in the description below, if the plural terminal devices 12, etc. need to be distinguished, the terminal device 12, the aroma emitting adapter 13, and the aroma cartridge 14 used by a member A are distinguished by the addition of a symbol at the end like the terminal device 12A, the aroma emitting adapter 13A, and the aroma cartridge 14A.

The messaging server device 11 is realized by having a general computer capable of data communication with another communication device via the Internet 19 execute the process according to an application program for a server according to this embodiment.

Figure 2:
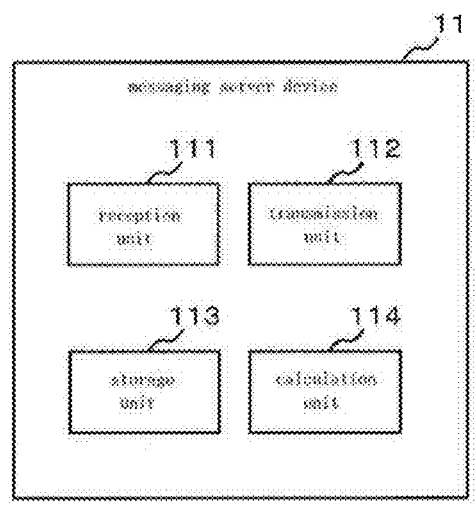
FIG. 2 is a block diagram depicting the outline of the function configuration of a messaging server device according to an embodiment of the present invention.

FIG. 2 is a block diagram of the outline of the function configuration of the messaging server device 11. In other words, a computer serving as the messaging server device 11 by executing the process based on the application program functions as a reception unit 111 receiving various data from the terminal devices 12 and the fortunetelling provision server device 15, a transmission unit 112 transmitting various data to the terminal devices 12 and the fortunetelling provision server device 15, a storage unit 113 storing various data such as the application program and databases described later, and a calculation unit 114 performing various processes such as the extraction of the terminal device 12 that satisfies the condition or the judgment on whether the message exchange is possible or not.

Note that each of these functions may be configured as a dedicated device realized by hardware, instead of realizing the messaging server device 11 by having the general computer execute the process based on the application program.

The messaging server device 11 may be configured as a group of devices in a manner that a plurality of devices disposed in different cases is operated in conjunction. For example, different kinds of processes to be executed by the messaging server device 11 may be executed in different devices, the same kind of process to be executed by the messaging server device 11 may be executed dispersedly in the plural devices, or processes sectioned area by area may be executed in different devices.

The terminal device 12 is realized by having a general computer such as a PDA (Personal Digital Assistant) having a telephone function, which is a so-called smartphone, a PDA not having a telephone function, a desktop PC (Personal Computer), or a laptop computer execute the process based on an application program for a terminal device according to this embodiment. Note that a part of the terminal device 12 has a function of acquiring positional data representing the current location of the terminal device 12 measured based on the intensity of the radio wave received from the terminal device 12 by a plurality of base stations included in a wireless communication network or a GPS (Global Positioning System).

Figure 3:
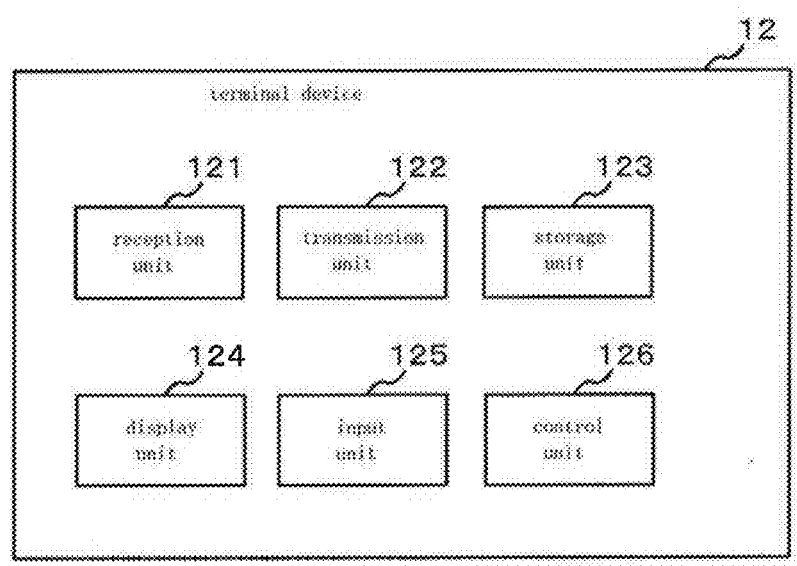
FIG. 3 is a block diagram depicting the outline of the function configuration of a terminal device according to an embodiment of the present invention.

FIG. 3 is a block diagram of the outline of the function configuration of the terminal device 12. A computer serving as the terminal device 12 by executing the process based on the application program functions as a reception unit 121 receiving various data from the messaging server device 11 and the fortunetelling provision server device 15, a transmission unit 122 transmitting various data to the messaging server device 11 and the fortunetelling provision server device 15, a storage unit 123 storing various data such as the application data and terminal identification data for identifying the own device, a display unit 124 displaying various information to a user, an input unit 125 accepting data input from the user by generating predetermined data in response to user operation, and a control unit 126 controlling the other configuration units of the own device and controlling the operation of the aroma emitting adapter 13.

Note that each of these functions may be configured as a dedicated device realized by hardware, instead of realizing the terminal device 12 by having the general computer execute the process based on the application program.

FIG. 4 is an external view of the aroma emitting adapter 13. FIG. 4(a) depicts the aroma emitting adapter 13 which is directly connectable to a data input/output terminal of the terminal device 12, and FIG. 4(b) depicts the aroma emitting adapter 13 which is connectable to the data input/output terminal of the terminal device 12 via a cable. In general, the type depicted in FIG. 4(a) is used for a PDA such as a smart phone, while the type depicted in FIG. 4(b) is used for a desktop PC or a laptop PC.

The number of aroma cartridges 14 that can be loaded in the aroma emitting adapter 13 at the same time is different depending on the type of the aroma emitting adapter 13; in this embodiment, the number is four at maximum. For example, the aroma emitting adapter 13 as depicted in FIG. 4(a) can have two aroma cartridges 14 loaded therein, and the aroma emitting adapter 13 as depicted in FIG. 4(b) can have four aroma cartridges 14 loaded therein at the same time.

The aroma emitting adapter 13 includes: a data input/output terminal 131 connected to the data input/output terminal of the terminal device 12 to exchange data therewith; a hollow part 132 receiving the aroma cartridge 14; a pressing pin (not shown) for pressing a button 142 of the aroma cartridge 14 loaded into the hollow part 132; a motor (not shown) applying force required to press down the button 142 to the pressing pin; a data reader (not shown) reading data from a memory chip 143 provided for an outer surface of the aroma cartridge 14; a light sensor (not shown) measuring the remaining amount of the aroma liquid contained in the aroma cartridge 14; and a microprocessor (not shown) transmitting and receiving data to and from the terminal device 12 and performing various controls including operation control of the motor.

Figure 5:
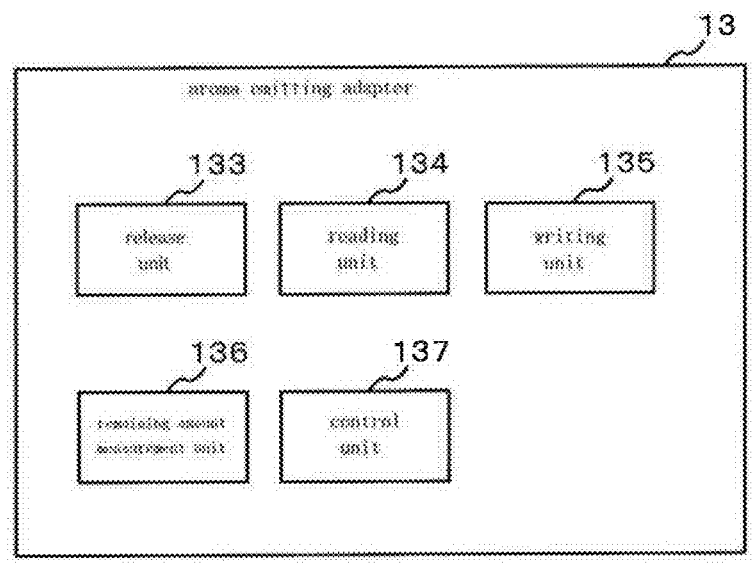
FIG. 5 is a block diagram depicting the outline of the function configuration of the aroma emitting adapter according to an embodiment of the present invention.

The aroma emitting adapter 13 functions as a device having a function configuration unit as depicted in FIG. 5 in accordance with a program installed in the microprocessor. In other words, the aroma emitting adapter 13 functions as: a release unit 133 externally releasing (spraying) the aroma liquid contained in the aroma cartridge 14 when the button 14 of the aroma emitting cartridge 14 is pressed down; a reading unit 134 reading the data from the memory chip 143 of the aroma cartridge 14; a writing unit 135 writing data in the memory chip 143 of the aroma cartridge 14; a remaining amount measurement unit 136 measuring the remaining amount of the aroma liquid contained in the aroma cartridge 14; and a control unit 137 controlling the process of these function configuration units.

FIG. 6 illustrates the appearance of the aroma cartridge 14. FIG. 6(b) is a diagram in which the aroma cartridge 14 illustrated in FIG. 6(a) is viewed from the opposite side.

The aroma cartridge 14 has the hollow part inside, in which the aroma liquid as the liquid having various kinds of aromas is enclosed. One end surface of the aroma cartridge 14 is provided with a spray hole 141 as a hole for releasing the aroma liquid out of the aroma cartridge 14. The spray hole 141 has a valve, which is open when a pressure of greater than or equal to a predetermined threshold is applied from the inside, so that the aroma liquid is swiftly sprayed out through the small hole and which is closed when the pressure applied from the inside is decreased to be less than the predetermined threshold, so that the aroma liquid is enclosed inside the aroma cartridge 14 again.

An end surface of the aroma cartridge 14, which is opposite to the end surface thereof provided with the spray hole 141, is provided with a button 142 that is pressed down by the pressing pin of the aroma emitting adapter 13. The button 142, while sealing the aroma liquid contained in the aroma cartridge 14, moves toward the inside of the aroma cartridge 14 following the force applied from the motor of the aroma emitting adapter 13 via the pressing pin. Along with the movement, the pressure in the aroma cartridge 14 is increased to release the aroma liquid from the aforementioned spray hole 141.

A top surface of the aroma cartridge 14 in FIG. 6 is provided with the memory chip 143 holding the cartridge identification data for identifying the aroma cartridge 14, the data representing the information related to the aroma liquid contained in the aroma cartridge 14, the data of the email address and the photo of the sender of the aroma cartridge 14, and the like. The memory chip 143 includes, for example, a flash memory chip that can hold various data including the cartridge IDs for identifying the aroma cartridge 14.

The cartridge ID corresponds to, for example, data based on the format of "####-######" (where "#" is any of 0 to F (hexadecimal number)). The first four numerals correspond to the cartridge type ID for identifying the type of the aroma cartridge 14 (specifically, the type of the aroma liquid contained in the aroma cartridge 14). The last six numerals correspond to the cartridge individual ID for identifying the individual aroma cartridge of the same type.

The memory chip 143 has a terminal on its external surface. Upon the loading of the aroma cartridge 14 into the hollow part 132 of the aroma emitting adapter 13, the terminal of the data reader of the aroma emitting adapter 13 is brought into contact with the terminal of the memory chip 143, is electrically connected thereto, and therefore the data readout from the memory chip 143 with the aroma emitting adapter 13 becomes possible. Therefore, the direction of the aroma cartridge 14 when inserted into the hollow part 132 is important, and in order to prevent a user from mistaking the direction, an inner surface of the hollow part 132 of the aroma emitting adapter 13 is provided with a ridge-like projection along the direction of the insertion and an outer surface of the aroma cartridge 14 (lower surface in FIG. 6) is provided with a groove-like recess along the direction of the insertion.

The fortunetelling provision server device 15 acquires various data on the aromas from the messaging server device 11, and distributes the fortunetelling data generated based on the various data related to the aromas to the terminal device 12 of the member of the instant messaging system 1 who wants the distribution of the fortunetelling information.

In a manner similar to the messaging server device 11, the fortunetelling information provision server device 15 is realized by having a general computer, which is capable of data communication with another communication device via the Internet 19, execute the process according to the application program for the server in this embodiment.

FIG. 7 is a block diagram depicting the outline of the function configuration of the fortunetelling information provision server device 15. In other words, the computer serving as the fortunetelling information provision server device 15 by executing the process based on the application program functions as: a reception unit 151 receiving various data transmitted from the terminal devices 12 and the messaging server device 11; a transmission unit 152 transmitting various data to the terminal devices 12 and the messaging server device 11; a storage unit 153 storing various data such as the application programs and the databases to be described later, etc.; and a calculation unit 154 performing various processes such as generation of fortunetelling data based on a predetermined condition.

Note that each of these functions may be configured as a dedicated device realized by hardware, instead of realizing the fortunetelling information provision server device 15 by having the general computer execute the process based on the application program. The fortunetelling information provision server device 15 may be configured as a group of devices in a manner that a plurality of devices disposed in different cases is operated in conjunction.

The storage unit 113 of the messaging server device 11 stores a user database as the database for managing the information related to the users, i.e., members of the instant messaging system 1, and a cartridge database as the database for managing the information related to each of various kinds of aroma cartridges 14 used in the instant messaging system 1. Examples of the data configuration of these databases are described below with reference to drawings.

FIG. 8 is a chart expressing the example of the data configuration of the user database stored in the messaging server device 11. The user database of the messaging server device 11 is a collection of records storing data related to each member of the instant messaging system 1. Each record of the user database of the messaging server device 11 includes the following fields.

"User ID": the ID (identifier) for identifying the member is stored.

"Password": the text data used for the identity verification of the member are stored.

"Terminal ID": in the case where the terminal device 12 of the member stores the ID uniquely assigned to the terminal device like the mobile phones that have recently come to be used widely, the assigned ID is stored. This terminal ID is used for verifying the identity of the member instead of the combination of the user ID and the password.

"Loaded cartridge ID": the ID (cartridge ID) uniquely assigned to the aroma cartridge 14 currently loaded in the terminal device 12 is stored.

"Remaining amount data": the value (%) representing the remaining amount of the aroma liquid contained in the aroma cartridge 14 currently loaded in the terminal device 12 is stored.

"Positional data": in the case where the terminal device 12 has a function of GPS, for example, to transmit the positional data representing the current location of the terminal device 12, the positional data are stored.

"Sex data": the data representing the sex of the member are stored.

"Age data": the data representing the age of the member are stored (however, the ages are expressed as "20's" or "30's" for the purpose of protecting personal information).

"Image data": the file names of the image data selected by the members such as the photos of the member and the picture or avatar of the member are stored. The original image data are stored in a predetermined location of the storage unit 113.

"Hobby data": the text data representing the hobby of the member are stored.

"Profile data": the text data representing the profile (such as self-advertisement) of the member are stored.

"Message friend judgment condition data": the condition data related to the user ID or the attribute data of the member with whom the member allows to exchange messages are stored. The attribute data of the member correspond to the general name of the data excluding "user ID", "password", and "terminal ID" from the fields included in the records stored in the user database of the messaging server device 11. If the condition data of "all members" are stored in this field, all the other members can transmit a message to this member.

"Calling friend judgment condition data": the condition data related to the user ID or the attribute data of the member with whom the member allows to have conversation are stored.

"Aroma emission log data": the cartridge ID of the aroma cartridge 14 containing the aroma liquid released in the past is stored together with the data representing date and the number of times of the releases of the aroma liquid.

"Message log data": the data related to the messages exchanged with another member in the past, for example the text data of the message, the use ID of the member with whom the message was exchanged, and the message exchange date are stored.

"Calling made and received log data": the data related to the conversation with another member in the past, for example, the user ID of the member with whom the conversation was made, and the date of the conversation are stored.

FIG. 9 is a chart expressing the example of the data configuration of the cartridge database stored in the messaging server device 11. The cartridge database is a collection of records storing data related to the types of the aroma cartridges 14 used in the instant messaging system 1. Each record of the aroma cartridge 14 includes the following fields.

"Cartridge type ID": the cartridge type ID is stored.

"Cartridge name data": the text data representing the name of the type of the aroma cartridge are stored.

"Aroma base name data": the text data representing the base of the aroma of the aroma liquid contained in the aroma cartridge (for example, "citrus-base", "oriental", "green-base", "floral-base", and "chypre-base") are stored.

"Access condition data": the condition data representing the condition related to the user ID or the attribute data of the member allowed to access through messaging or calling while this aroma cartridge is loaded are stored. For example, as the condition data stored in this field, "pair ID->message exchange allowed" is given which means the message exchange is allowed between the aroma cartridge whose cartridge individual ID number is an odd number and the aroma cartridge whose cartridge individual ID number is the next even number.

"Aroma explanation data": the text data representing the description related to the composition, effect, and the like of the aroma liquid contained in the aroma cartridge are stored.

The storage unit 153 of the fortunetelling information provision server device 15 stores the user database as the database for managing the information related to the members who want to have the fortunetelling information related to the aroma (members registered in the fortunetelling information provision server device 15).

FIG. 10 is a chart expressing the example of the data configuration of the user database stored in the fortunetelling information provision server device 15. The user database of fortunetelling information provision server device 15 is a collection of records storing the data related to the members who want to receive the fortunetelling information among the members using the instant messaging system 1. Each record of the user database of the fortunetelling information provision server device 15 includes the following fields.

"User ID": the ID for identifying the member is stored.

"Password": the text data for verifying the identity of the member are stored.

"Email address": the email address as the address of the email at which the user of the terminal device 12 can receive the email (destination to which the fortunetelling information is transmitted).

1. 2. Operation

Next, the operation of the instant messaging system 1 is described. The member of the instant messaging system 1 registers his/her user ID and password (user registration) for the messaging server device 11 using his own terminal device 12. On this occasion, if the terminal ID is recorded in the terminal device 12 and the transmission thereof is possible, the terminal device 12 transmits the terminal ID of its own terminal device to the messaging server device 11. The terminal ID transmitted in this manner is registered in a new record of the user database (see FIG. 8) with the user ID and the password.

The member installs the application program for the instant messaging in the terminal device 12 in advance. The application program for the instant messaging installed in the terminal device 12 is hereinafter referred to as "messaging app".

For using the instant messaging system 1, the member needs to prepare the aroma emitting adapter 13 and at least one aroma cartridge 14. The member is ready for the message exchange and the conversation in the instant messaging system 1 by connecting the aroma emitting adapter 13 to the terminal device 12 and loading the aroma cartridge 14 in the aroma emitting adapter 13.

After the above preparation, the member activates the messaging app on the terminal device 12. Alternatively, the user may set so that the activation of the terminal device 12 automatically triggers the activation of the messaging app and makes the messaging app reside.

Note that when the messaging app is activated, the terminal device 12 checks if the aroma emitting adapter 13 is connected or not according to the messaging app. If the aroma emitting adapter 13 is connected, the terminal device 12 performs data communication with the aroma emitting adapter 13 and checks if the aroma emitting cartridge 14 is loaded in the aroma emitting adapter 13. As a method of checking the loading of the aroma emitting cartridge 14 in the aroma emitting adapter 13, a method of checking the loading based on whether the data can be read from the memory chip 143 of the aroma cartridge 14 or not, a method of checking the loading based on the measurement result from the remaining amount measurement unit 136, and other various methods are given.

If the aroma emitting adapter 13 is not connected to the terminal device 12 or the aroma cartridge 14 is not loaded in the aroma emitting adapter 13, the terminal device 12 notifies it to the member by displaying an error message on the display unit 124 and then cancels the activation of the messaging app. In other words, in this embodiment, the loading of the aroma cartridge 14 is necessary in using the messaging app. Therefore, if the aroma emitting adapter 13 is removed from the terminal device 12 or all the aroma cartridges 14 are removed from the aroma emitting adapter 13 during the activation of the messaging app, the messaging app is automatically ended.

In the case where the aroma emitting adapter 13 is connected and the aroma cartridge 14 is loaded, the terminal device 12 subsequently performs the process of verifying the identity of the member as a step of activating the messaging app. Specifically, the app demands the input of the user ID and the password from the user and transmits the input data to the messaging server device 11. By comparing the user ID and the password received from the terminal device 12 with the data in the user database (see FIG. 8), the identity of the member is verified.

If the terminal device 12 can transmit the terminal ID, the terminal ID can be used for verifying the identity instead of inputting the user ID and the password by the setting of the terminal ID in the messaging app. In this case, the terminal device 12 transmits the terminal ID to the messaging server device 11 upon the activation of the messaging app and the identity verification by comparison of the terminal ID is performed in the messaging server device 11.

When the identity is verified, the member can log onto the messaging server device 11. In the logged-on state, the messaging app displays a screen including a plurality of tab pages in the display unit 124 of the terminal device 12. FIG. 11 to FIG. 17 schematically depict the tab pages.

The screen of the messaging app includes, for example, the following tab pages.

"Message": tab for exchanging message with another member.

"calling": tab for having conversation with another member.

"Ranking": rank of the aroma cartridges in the order of most frequently emitted aroma recently, and rank of the members who have most frequently performed the aroma emission recently.

"Aroma map": tab indicating the current locations of the members on the map with the patterns representing the aroma base of the aroma cartridge currently loaded by the member of the instant messaging system 1 (user of the terminal device 12 that can transmit the positional data).

"Member information": tab for displaying the cartridge name of the aroma cartridge 14 currently used by the member (loaded in the aroma emitting adapter 13) and the aroma cartridge 14 used in the past, the remaining amount and the number of aroma emissions, and the rank of the members based on the number of aroma emissions.

"Cartridge information": tab for displaying the cartridge name of the aroma cartridge 14 currently loaded, the name of the aroma base, the explanation of the aroma, and the message.

"Utility": tab for setting for allowing the own terminal to emit aroma at a predetermined time or in the occurrence of a predetermined event.

Figure 11:
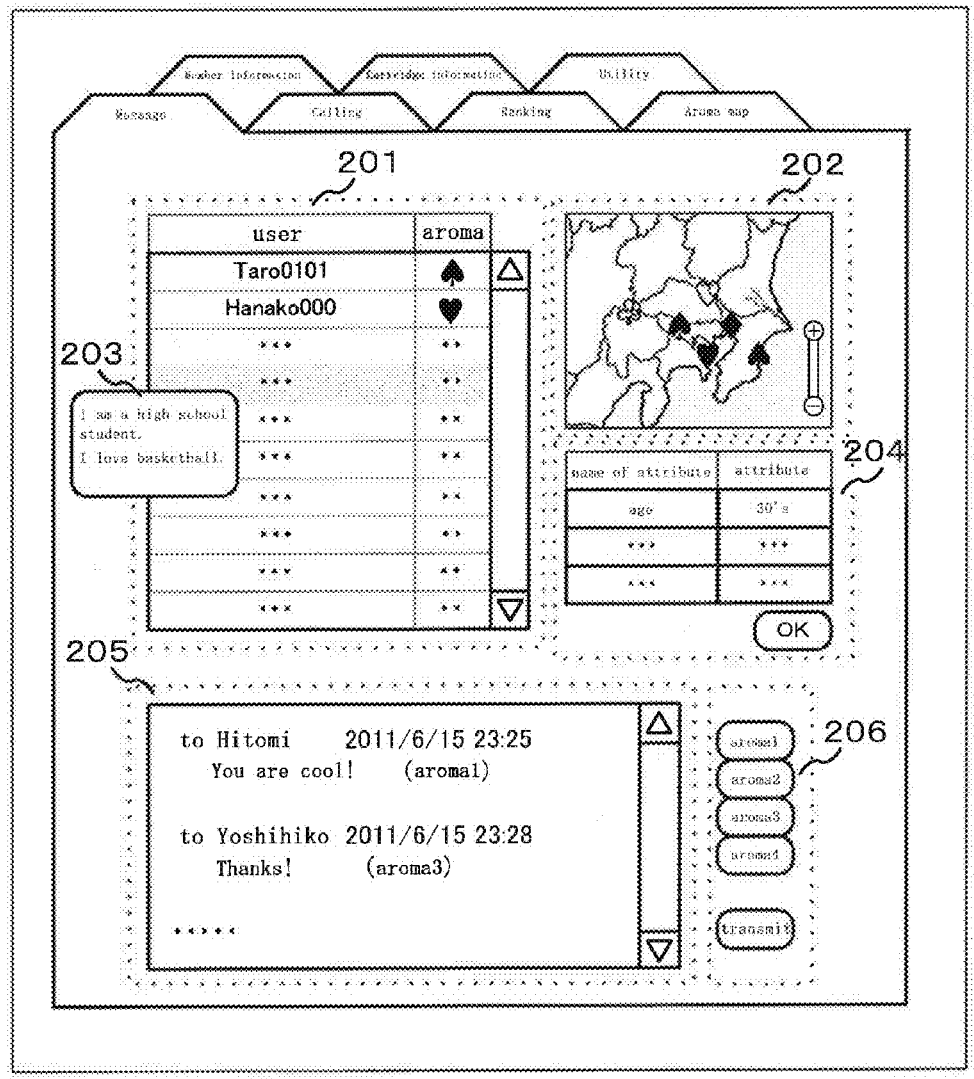
FIG. 11 schematically depicts a screen of a "message" tab displayed on a terminal device according to a messaging app according to an embodiment of the present invention.

FIG. 11 schematically depicts the screen of the "message" tab. A region 201 of the "message" tab displays user names of members (hereinafter referred to as "other members") with whom a member (hereinafter referred to as "user" and distinguished from the other members) allows to exchange message and who is currently logged onto the messaging server device 11, and moreover the aroma base name of the aroma cartridge 14 currently loaded in the aroma emitting adapter 13 of each member. The order of displaying the other members may be, in the case where the terminal device 12 can transmit the positional data, the order of the members being closer to the user, for example.

A region 202 of the "message" tab displays patterns according to the aroma base plotted on the map in accordance with the current location of the other members displayed on the region 201 (limited to the members with the terminal devices 12 having the function of transmitting the positional data).

When the user selects, by clicking or the like, the user name of the other member displayed in the region 201 or the pattern plotted on the region 202, a window 203 pops up and displays the cartridge name of the aroma cartridge 14 currently loaded in the aroma emitting adapter 13 or the profile of the selected other member. If the terminal device 12 of the selected other member is capable of transmitting the positional data, the display position on the map is automatically changed to show the current location of the other member at the center of the map and the pattern corresponding to the selected member is highlighted.

A region 204 of the "message" tab displays a box where the user inputs the condition for narrowing the other members displayed in the regions 201 and 202. For example, the user inputs "age" in the "attribute name" box and "30's" in the "attribute" box in the region 204 and then clicks "OK". Thus, the user can display only the other members in 30's in the regions 201 and 202 among the other members who are allowed to transmit a message to the user. By designating the combination of the attribute name and the attribute in these boxes, the user can easily find the person to whom the user wants to transmit the message.

The user selects one or more user names of the other members or patterns corresponding to the other members in the region 201 or the region 202, inputs the message in a region 205, and then clicks "transmit" displayed in a region 206, thereby transmitting the message to the selected member. Since known various techniques are applicable in this message transmission system, the detailed description is omitted.

The user can add the instruction of aroma emission in the transmission message by, for example, clicking any of "aroma 1" to "aroma 4" buttons displayed in the region 206. For example, if "aroma 1" is clicked in addition to the input of the message, the message having the aroma emission instruction "Will you be working late again today? Take it easy! (aroma 1)" is generated. Upon the click of the "transmit" in this state, the data representing the message having the aroma emission instruction (message data and aroma emission instruction data) are transmitted to the terminal device 12 of the other member as the destination of the message from the terminal device 12 of the user via the messaging server device 11.

Upon the reception of the message data and the aroma emission instruction data, the terminal device 12 of the other member displays the message in the region 205 according to the received message data, and instructs the aroma emitting adapter 13 to release the aroma liquid in accordance with the aroma emission instruction data. The aroma emitting adapter 13 presses down the button 142 of the aroma cartridge 142 designated by the instruction, thereby releasing the aroma liquid from the spray hole 141. As a result, the other member receives the message with aroma from the user. Here, the aroma also serves as the notification of the incoming message.

Note that the "aroma 1" button corresponds to the first aroma cartridge 14 loaded in the aroma emitting adapter 13 of other member to whom the message is transmitted, and the "aroma 2" button corresponds to the second aroma cartridge 14 loaded in the aroma emitting adapter 13 of the other member to whom the message is transmitted, and so on. Therefore, among "aroma 1" to "aroma 4" buttons, the button available is automatically selected and the unavailable button is displayed in gray depending on where the aroma cartridge 14 is loaded in the aroma emitting adapter 13 of the other member to whom the message is transmitted. Note that when the message is transmitted to the multiple other members, only "aroma 1" button is available and the user who transmits the message cannot choose the aroma.

Figure 12:
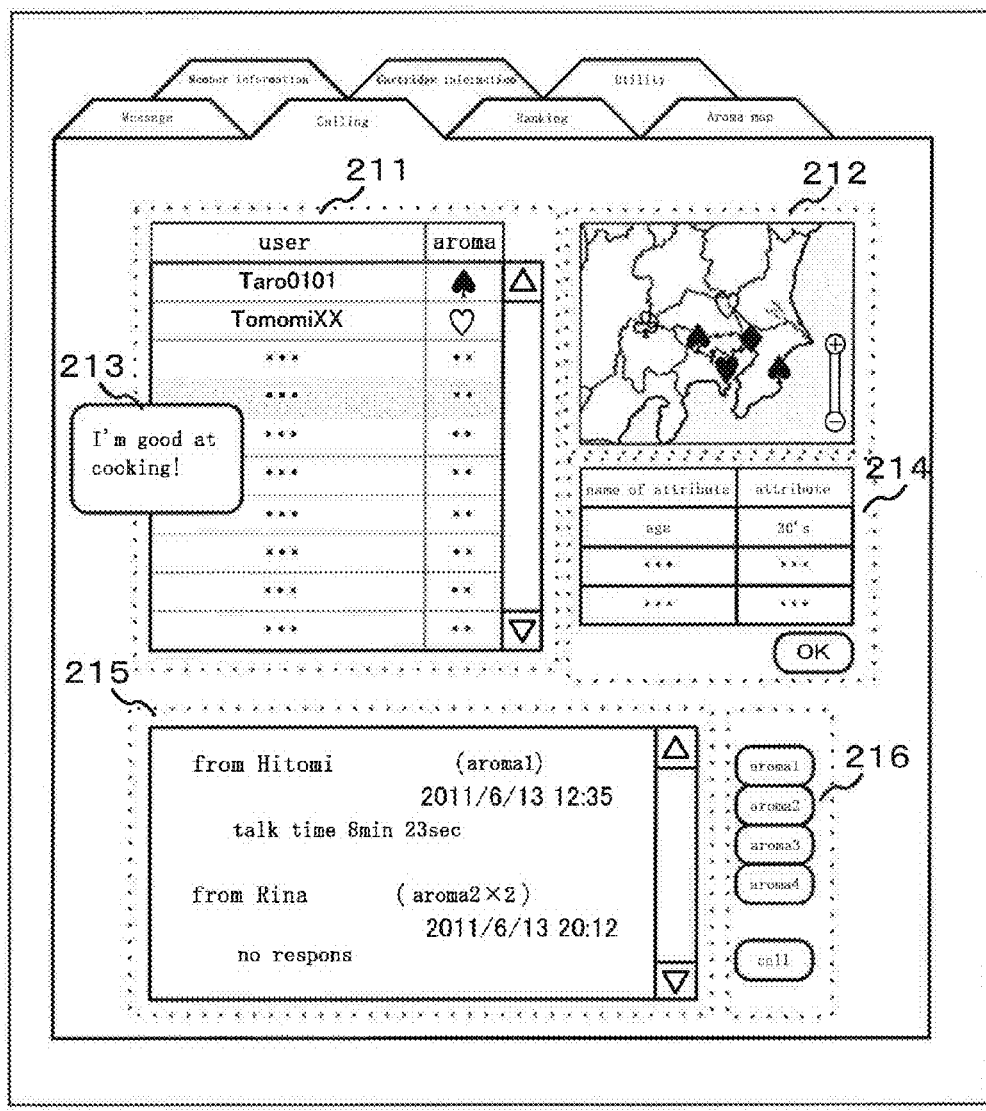
FIG. 12 schematically depicts a screen of a "calling" tab displayed on the terminal device according to the messaging app according to an embodiment of the present invention.

FIG. 12 is a schematic diagram of the "calling" tab screen. The "calling" tab screen includes approximately the same objects as the "message" tab, and regions 211, 212, a window 213, and a region 214 of the "calling" tab have the similar functions to the regions 201, 202, the window 203, and the region 204 of the "message" tab, respectively.

A region 215 of the "calling" tab corresponds to the region 205 of the "message" tab; however, the region 205 of the "message" tab displays the log of the exchanged messages while the region 215 of the "calling" tab displays the log of the calling such as the calling received time, disconnected time, and conversation period of time.

A region 216 of the "calling" tab corresponds to the region 206 of the "message" tab; however, the region 216 of the "calling" tab includes a "calling" button instead of the "transmit" button of the "message" tab.

The user clicks twice the "aroma 1" button and then clicks the "calling" button, for example. In response to this operation, the data instructing the calling with the aroma emission instruction (calling data and aroma emission instruction data) are transmitted from the terminal device 12 of the user to the terminal device 12 of the other member at the calling destination via the messaging server device 11. The aroma emission instruction data in this case are the data instructing that the aroma liquid is released twice.

Upon the reception of the calling data and the aroma emission instruction data, the terminal device 12 of the other member performs a predetermined calling operation such as sound emission or vibration in accordance with the received calling data, and instructs the aroma emitting adapter 13 to release the aroma liquid twice in accordance with the aroma emission instruction data. The aroma emitting adapter 13 presses the button 142 of the aroma cartridge 14 designated by the instruction twice to release the aroma liquid from the spray hole 141. As a result, the other member is notified of the calling by the aroma in addition to the calling sound from the user. Since the operation of the terminal device 12 and the messaging server device 11 is similar to that of a known calling system via the Internet, the description is omitted.

Figure 13:
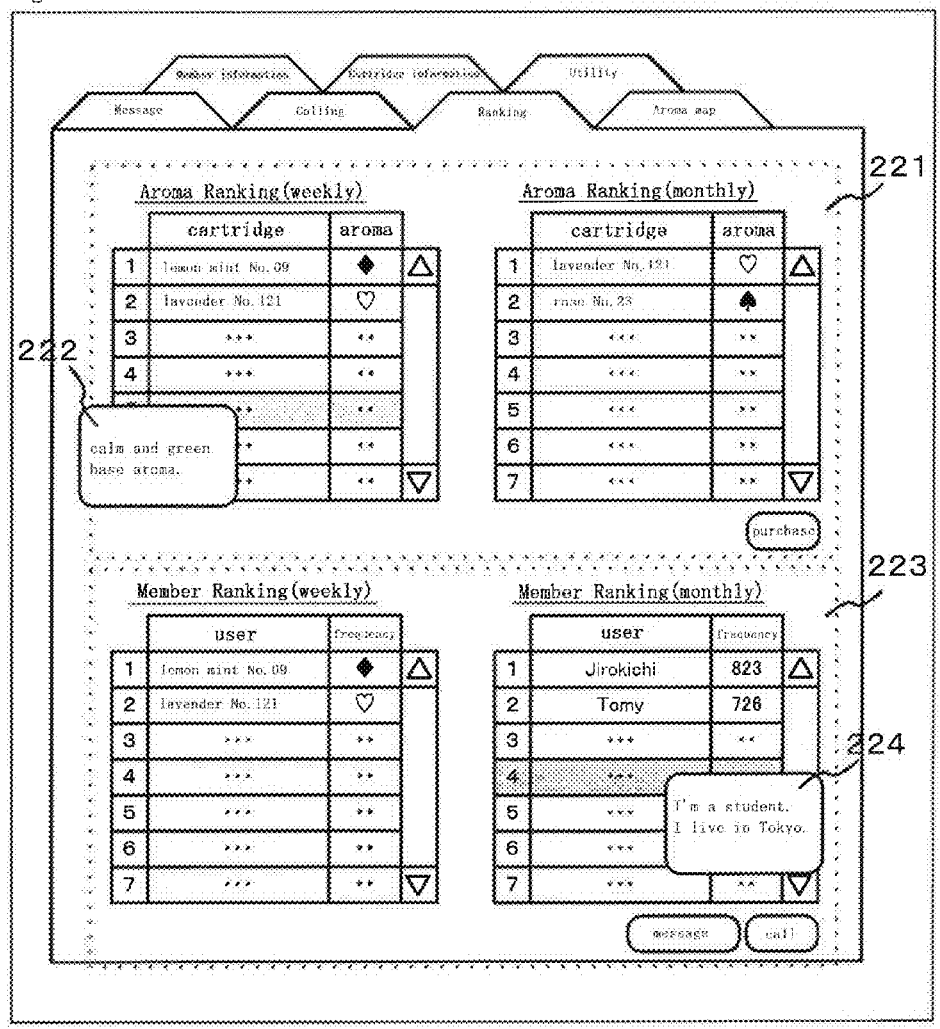
FIG. 13 schematically depicts a screen of a "ranking" tab displayed on the terminal device according to the messaging app according to an embodiment of the present invention.

FIG. 13 is a schematic diagram of the screen of the "ranking" tab. A region 221 of the "ranking" tab displays the rank of aromas in the order of most frequently used by all the members of the instant messaging system 1 in a past week or month. Upon the selection of the cartridge name displayed in the ranking by the user, the information of the aroma cartridge 14 corresponding to the selected cartridge name pops up in a window 222.

The region 221 includes a "purchase" button. When the user selects any of the cartridge names displayed in the ranking and then clicks this "purchase" button, the user can purchase the aroma cartridge 14 corresponding to the selected cartridge name. Since the process of purchasing the aroma cartridge 14 is similar to the process of a known Internet shopping system, the description is omitted.

A region 223 displays the members of the terminal devices 12 in the order of using the aroma liquid most frequently in a past week or month. Upon the selection of the user name displayed in the ranking by the user, the information of the member corresponding to the selected user name pops up in a window 224.

The region 223 includes a "message" button and a "calling" button. If the user selects the user name of the other member to whom the user is allowed to transmit the message among the user names displayed in the ranking, the "message" button becomes available, and if the user selects the user name of the other member with whom the user is allowed to have a conversation, the "calling" button becomes available. By clicking the available "message" button or "calling" button, for example, the user can transmit the message to, or make a call to the other member corresponding to the selected user name.

Specifically, if the "message" button is clicked, for example, the display of the "ranking" tab in the terminal device 12 is automatically switched to the display of the "message" tab, and if the "calling" button is clicked, for example, the display of the "ranking" tab in the terminal device 12 is automatically switched to the display of the "calling" tab. In the tab after the switch, the user can transmit the message with the aroma emission instruction to, or make a call with the aroma emission instruction to the other member selected in the "ranking" tab.

Figure 14:
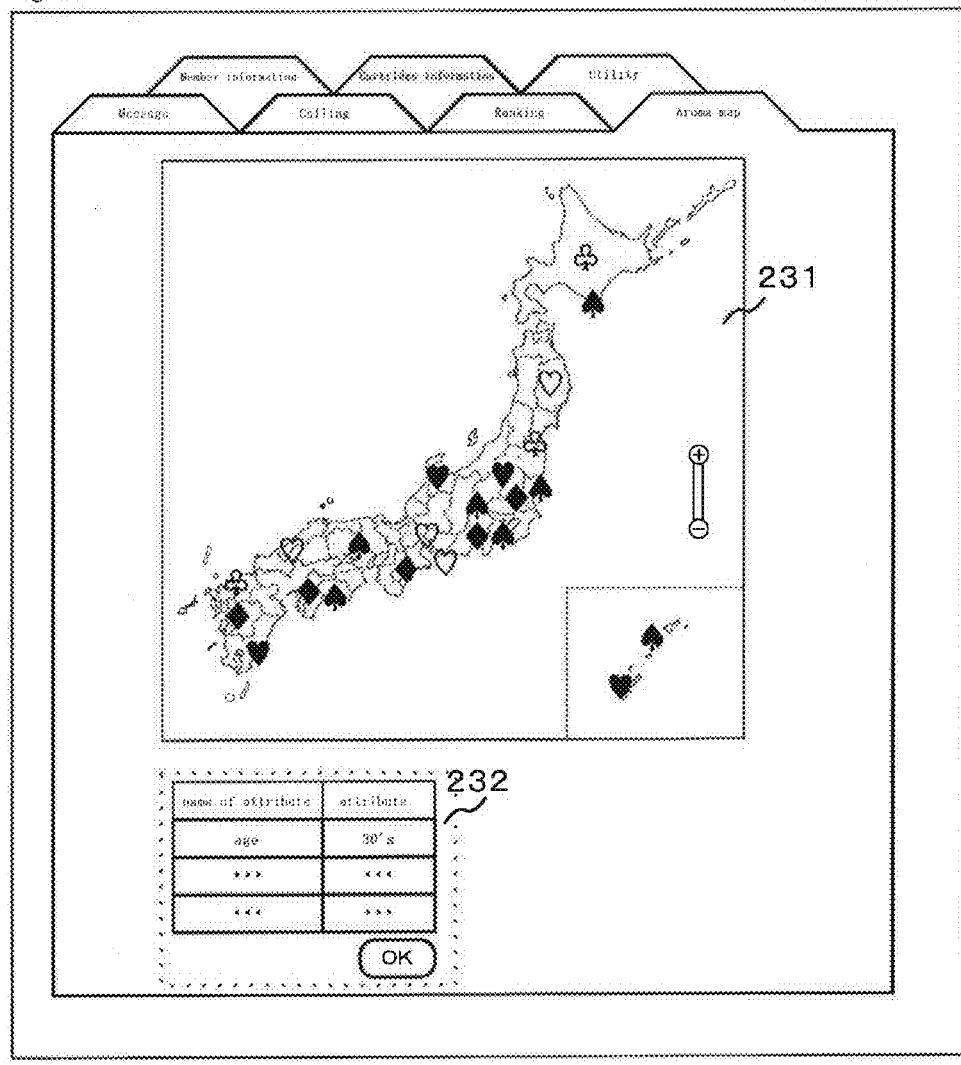
FIG. 14 schematically depicts a screen of an "aroma map" tab displayed on the terminal device according to the messaging app according to an embodiment of the present invention.

FIG. 14 is a schematic diagram of the screen of the "aroma map" tab. A region 231 of the "aroma map" tab displays a map in which patterns corresponding to the aroma bases of the aroma cartridges 14 currently loaded are plotted at the positions of the members who are currently logged on (limited to the members of the terminal devices 12 capable of transmitting the positional data).

A region 232 displays boxes to which the conditions for narrowing the patterns displayed on the map of the region 231 are input. A method of using these boxes is similar to the method of using the boxes displayed in the region 204 of the "message" tab. When the user inputs the appropriate attribute name and attribute in these boxes and then clicks "OK", the user can know the information on the type of aroma in the aroma cartridge 14 used by the member group having the user's selected attribute, along with its geographic information.

Figure 15:
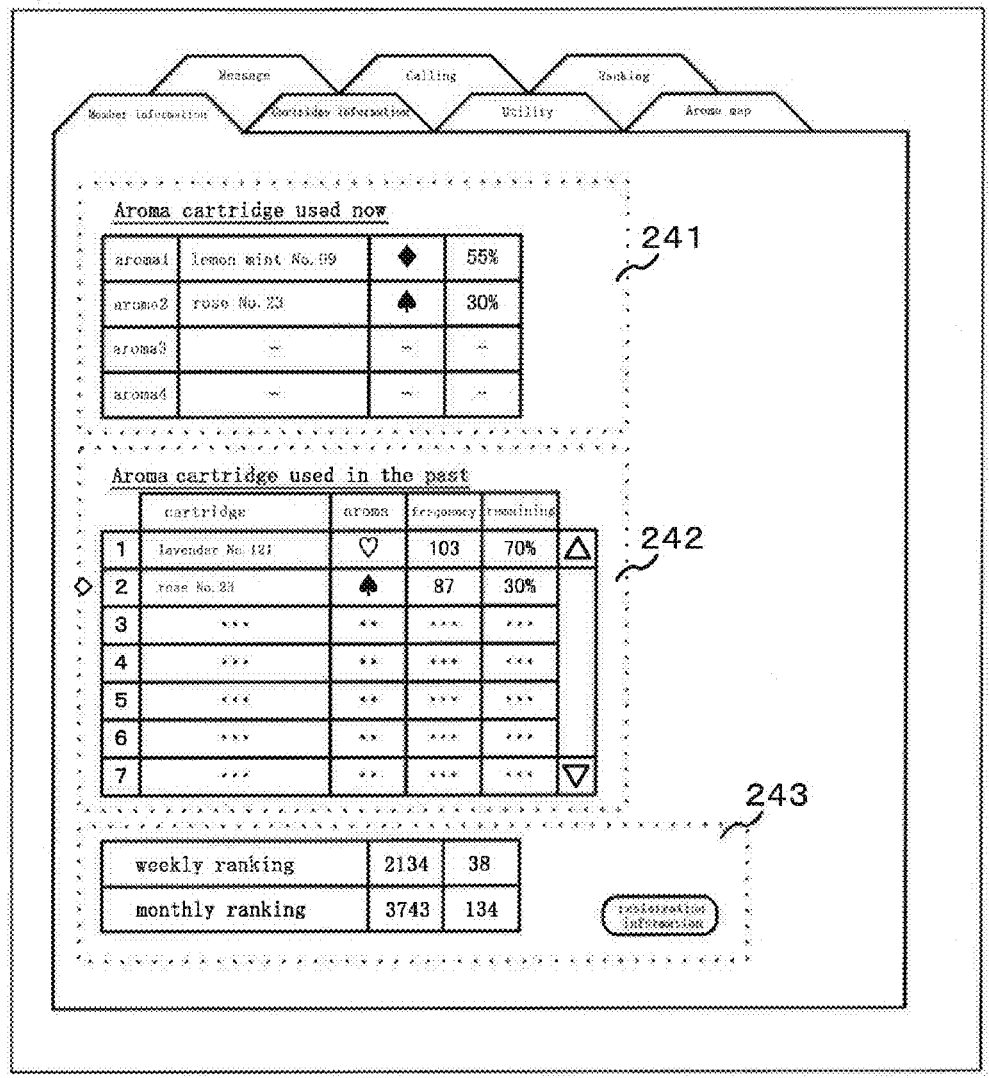
FIG. 15 schematically depicts a screen of a "member information" tab displayed on the terminal device according to the messaging app according to an embodiment of the present invention.

FIG. 15 is a schematic diagram of the screen of the "member information" tab. A region 241 of the "member information" tab displays the cartridge name and the remaining amount (%) of the aroma cartridge 14 currently loaded in the aroma emitting adapter 13 of the user.

A region 242 of the "member information" tab displays a list of the cartridge names and the number of times of aroma emissions of the aroma cartridges 14 used by the user in the past. In the list displayed in the region 242, the aroma cartridge 14 currently loaded is marked to be distinguished.

A region 243 of the "member information" tab displays the ranking of a week or a month based on the number of times of the aroma emissions of the user. The region 243 includes a "registration information" button, and if the user clicks the "registration information" button, the page for viewing or correcting the registration information is opened so that the user can confirm the information such as the registered profile or correct the profile as necessary.

Figure 16:
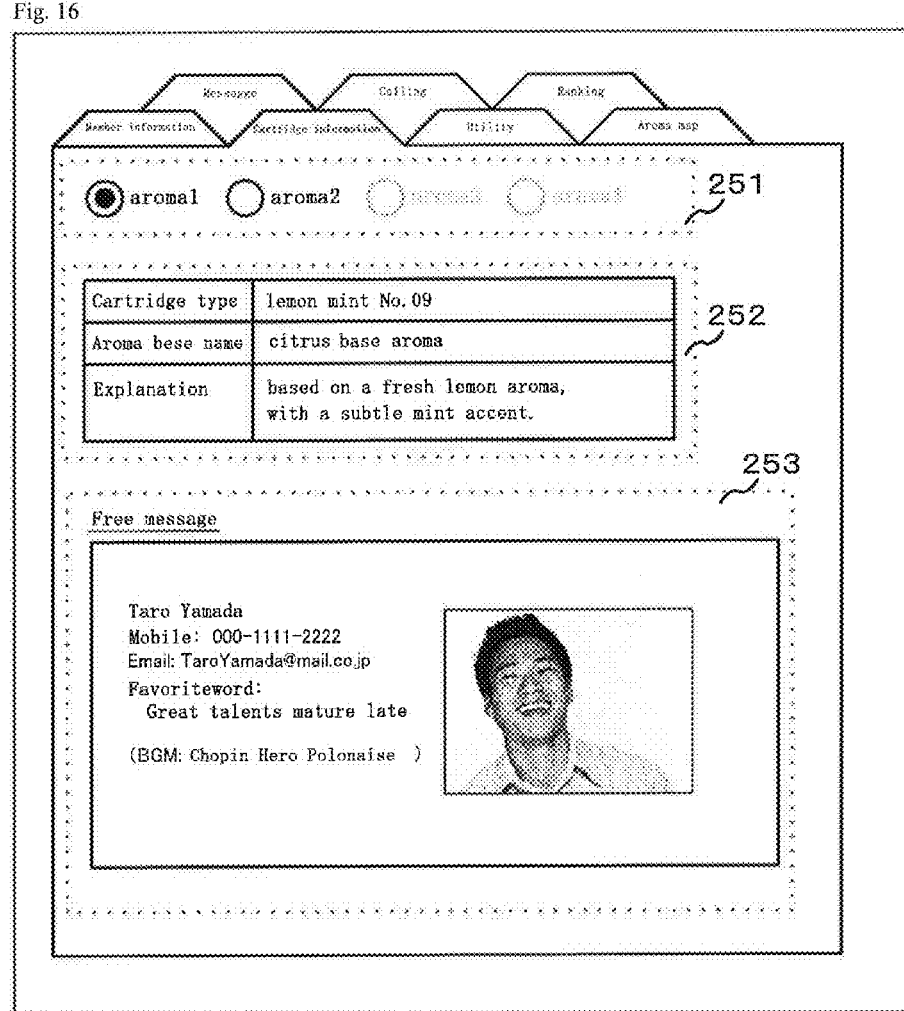
FIG. 16 schematically depicts a screen of a "cartridge information" tab displayed on the terminal device according to the messaging app according to an embodiment of the present invention.

FIG. 16 is a schematic diagram of the screen of the "cartridge information" tab. A region 251 of the "cartridge information" tab displays check boxes for allowing the selection of the aroma cartridge 14 for which the information is displayed. A region 252 of the "cartridge information" tab displays the information such as the aroma base name of the aroma cartridge 14 currently loaded.

A region 253 of the "cartridge information" tab displays various messages or images (still images or moving images). These images may be accompanied by sound such as voice or music. The display or sound is made in accordance with the data read out from the memory chip 143 of the aroma cartridge 14 by the reading unit 134 of the aroma emitting adapter 13.

In other words, manufacturers, sellers, or general users of the aroma cartridges 14 can provide various information, for example, transmit messages, show still or moving images, play music, tell voice message, etc. to the member using the aroma cartridge 14 by freely writing various data such as messages, still image data, moving image data, voice data, and the application programs to the aroma cartridges 14 from the PC or the terminal device 12 through a data reader/writer for the memory chip 143 of the aroma cartridge 14 or the writing unit 135 of the aroma emitting adapter 13 connected to the terminal device 12.

Therefore, the member can use the aroma cartridge 14 in various ways; for example, the member records the data such as his own name, photo, address of the company, and email address in the aroma cartridge 14 and distributes the aroma cartridge 14, whereby the member can use the aroma cartridge 14 as a business card, or the member records romantic music with the message for a proposal and sends the aroma cartridge 14 to a lover as a love letter.

For example, a member who is an owner of a flower shop can record the data of the shop and the flower recommended for the month in the aroma cartridge 14 containing the original floral-base aroma liquid, and distributes the cartridge 14 to customers or potential customers. As another example, a member who is an owner of a noodle shop can record the data of the shop and the image of noodles in the aroma cartridge 14 containing the noodle aroma liquid, and distributes the cartridge 14 to customers or potential customers. Thus, the aroma cartridge 14 can be utilized as an advertisement medium.

As another example, a game developing and selling company can record a program of a game involving the aroma emission in the aroma cartridge 14 and sell the aroma cartridge 14, so that the aroma cartridge 14 is used as a sales medium. In this case, the game program may be configured so as to be installed in the terminal device 12 automatically in accordance with an automatic execution program recorded in the memory chip 143 when the aroma cartridge 14 is loaded for the first time in the aroma emitting adapter 13 connected to the terminal device 12.

Further, by loading the plural correlated aroma cartridges 14 at the same time, the terminal device 12 can perform the linking process in accordance with the program of the game recorded in each of them. In this case, the function of the game that cannot be realized by the single aroma cartridge 14 becomes available. Note that the program recorded in the aroma cartridge 14 and executed by the terminal device 12 is not limited to the game program but may be a program for business use.

Figure 17:
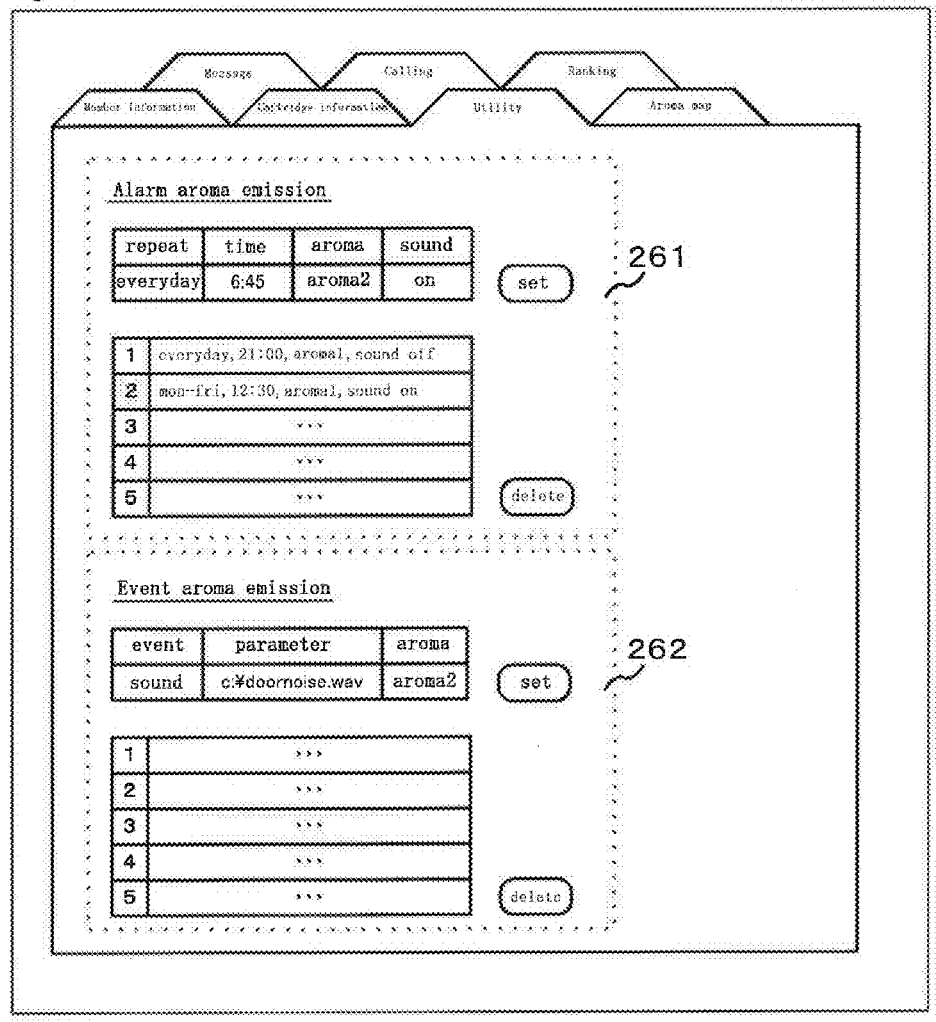
FIG. 17 schematically depicts a screen of a "utility" tab displayed on the terminal device according to the messaging app according to an embodiment of the present invention.

FIG. 17 is a schematic diagram of the screen of the "utility" tab. A region 261 of the "utility" tab displays the input box and a "set" button for setting the alarm aroma emission that allows the own device to emit the aroma automatically at a designated time, and a list of the alarm aroma emissions and a "delete" button for deleting the setting from the list.

If the user inputs the parameters of the alarm aroma emission in the input box in the region 261, for example, "every day, 6:45, aroma 2, with sound" and then clicks the "set" button, the user can set the alarm aroma emission. Since the data representing these settings are not used by the other member, the data are stored in the storage unit 123 of the terminal device 12. The user can delete the selected setting by selecting any setting from the list and then clicking the "delete" button, for example.

The control unit 126 of the terminal device 12 instructs the aroma emitting adapter 13 to release the aroma liquid from the aroma cartridge 14 with the set number when the time acquired from the timer device of the own device comes. As a result, at the designated time, the aroma is emitted from the designated aroma cartridge 14.

A region 262 of the "utility" tab displays the input box and the "set" button for the setting of the event aroma emission, that allow the own device to emit the aroma automatically in the occurrence of a particular event, and a list of the event aroma emissions already set and a "delete" button for deleting the setting from the list.

The user inputs the parameters of the event aroma emission in the input box in the region 262, for example, "sound (file name of sound data), aroma 1", and clicks the "set" button, whereby the event aroma emission can be set. Since the data representing these settings are not used by the other member, the data are stored in the storage unit 123 of the terminal device 12. The user can delete the selected setting by selecting any setting from the list and then clicking the "delete" button, for example.

The parameters "sound (file name of sound data), aroma 1" are the parameters for instructing the aroma emitting adapter 13 to release the aroma liquid from the first aroma cartridge 14 in the case where the sound similar to the sound represented by the sound data designated by the file name is collected with the terminal device 12a incorporated with a microphone. The user, for example, can designate the sound data obtained by recording the sound of opening a door and set the parameters as above, and then place the terminal device 12 to which the aroma emitting adapter 13 having the aroma cartridge 14 loaded therein is connected near the door; so that when someone opens the door, the aroma can be emitted.

Various events can be considered that can be used for the event aroma emission. For example, the image data can be set as the parameters of the event aroma emission in the terminal device 12 incorporating a camera. This makes it possible to emit aroma when the camera of the terminal device 12 photographs a similar image. As another example, the aroma can be emitted when the terminal device 12 having a touch panel display is rubbed or the terminal device 12 having an accelerometer is shaken.

The description has been made of the structure of the screens of the messaging app and the operation of the user on the screens. Various necessary data are exchanged between the terminal device 12 and the messaging server device 11 in response to the opening and closing of the screen, the operation of the user in each tab, and the like. Moreover, as necessary, the data read from the aroma cartridge 14 by the aroma emitting adapter 13 are acquired from the aroma emitting adapter 13 by the terminal device 12.

For example, when the "message" tab is opened in the terminal device 12 of the user, the messaging server device 11 reads out the user names and the positional data, etc. of the user and other members from the user database (see FIG. 8), reads out the aroma base names and the like corresponding to these user names from the cartridge database (see FIG. 9), and transmits the data to the terminal device 12. With the use of the data received from the messaging server device 11, the terminal device 12 displays the list in the region 201 and the map in the region 202.

Upon the input of the data representing the condition in the input box in the region 204 from the user, the data are transmitted from the terminal device 12 to the messaging server device 11, where the extracting process is performed. Thus, the user names and their positional data related to the extracted members are transmitted from the messaging server device 11 to the terminal device 12. As a result, the region 201 and the region 202 display only the information of the members satisfying the designated condition.

For example, when the "cartridge information" tab is opened in the terminal device 12 of the user, the aroma emitting adapter 13 reads out the data stored in the memory chip 143 of the aroma cartridge 14, and sends the readout data to the terminal device 12. As a result, the various data are displayed as depicted in FIG. 16.

For enabling the display of the screen of the messaging app as aforementioned in the terminal device 12, various kinds of processes are necessary: for example, the data transmission process from the terminal device 12 to the messaging server device 11; the searching process in the messaging server device 11; the data transmission process from the messaging server device 11 to the terminal device 12; the data reading process from the aroma cartridge 14 by the aroma emitting adapter 13; the data transfer process from the aroma emitting adaptor 13 to the terminal device 12, and the generation process for the display image data in the terminal device 12. Since these processes are well known to a person skilled in the art, the description is omitted.

In the instant messaging system 1, the user can receive the provision of the information of another member based on the data managed in the messaging server device 11 as above, and receive the provision of additional information from the various information provision server devices different from the messaging server device 11. The fortunetelling information provision server device 15 is an example of such information provision server devices.

The user registers his/her information on the website with a predetermined URL through the terminal device 12 in advance. Specifically, the user registers the same user name and password as those registered in the messaging server device 11 and additionally registers the email address to which the fortunetelling information is distributed. Those pieces of data are stored in the user database of the fortunetelling information provision server device 15 (see FIG. 10).

The fortunetelling information provision server device 15 generates the extraction condition data including the user IDs and their passwords registered in the user database of the device 15 (see FIG. 15) and transmits the generated extraction condition data to the messaging server device 11 every day at a predetermined time, for example. The messaging server device 11 searches the user database (see FIG. 8) for the record including the user ID included in the received extraction condition data. Further, the messaging server device 11 extracts the cartridge type ID of the aroma cartridge 14 recently loaded from the aroma emission log data in the found record and searches the cartridge database (see FIG. 9) for the record including the extracted cartridge type ID. The messaging server device 11 transmits the data included in the record of the user database and the cartridge database found thus to the fortunetelling information provision server device The fortunetelling information provision server device 15 generates, for each type of the aroma cartridge 14 to be loaded, the data (fortune data) representing the fortune of the day for the user according to a predetermined algorithm on the basis of the attribute of the user (such as sex, age, hobby, current location, and the aroma cartridge 14 currently loaded) known from the data transmitted from the messaging server device 11.

The fortunetelling information provision server 15 generates the email containing the fortune data generated thus, and sends the email via the Internet 19 to the email address of the user stored in the database of the device 15 (see FIG. 10). The email sent is received by the terminal device 12 of the user via an email server device through a known email distribution mechanism.

Figure 18:
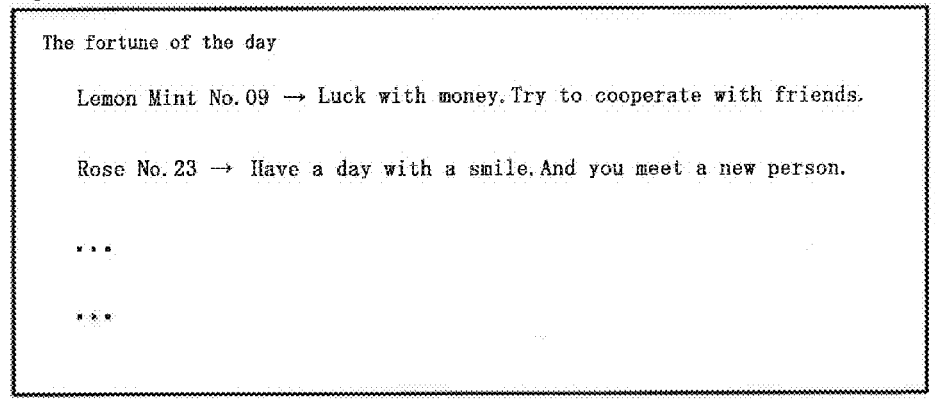
FIG. 18 schematically depicts the content of the email received from the fortunetelling information provision device by the terminal device according to an embodiment of the present invention.

FIG. 18 schematically depicts the content of the email received from the fortunetelling information provision server device 15 by the terminal device 12. The user can know the fortune of the day for every aroma cartridge 14 of his/her own, according to the email transmitted from the fortunetelling information provision server device 15. Therefore, with reference to the fortunes, the user can select the aroma cartridge 14 to be loaded in the aroma emitting adapter 13 on that day.

In this manner, the instant messaging system 1 according to this embodiment can provide various kinds of information on the aroma such as the currently popular aroma, while enabling the exchange of the message and conversation along with the aroma between the user and another user. This makes the information exchange via the network more fun.

2. Modified Example

Various modifications can be made in the range of technical ideas of the present invention. The modified example is described below.

In the above embodiment, the aroma is emitted from the terminal device 12 in accordance with the message exchange or the voice call made in real time; however, the present invention is not limited thereto. For example, the aroma may be emitted upon the reception of the email.

In the above embodiment, the aroma emitting adapter 13 is connected as an external device to the terminal device 12; however, the aroma emitting adapter 13 may be incorporated in the terminal device 12.

As described above, the fortunetelling information provision server device 15 in the above embodiment is an example of the information provision server devices distributing the additional information to the member based on the attribute data of the member and the attribute data of the aroma cartridge 14 provided from the messaging server device 11, and other various kinds of information can be given as the information provided from such information provision server devices.

As other examples of the additional information, the following are given: a list of members considered to have affinity among the members currently logged onto the instant messaging system 1 on the basis of the information such as the sex, the age, and the aroma cartridge 14 currently loaded; and the type of the aroma cartridge 14 recommended based on the current temperature or weather.

In the case of the above examples, the information provision server device transmits to the messaging server device 11, not just the user name of the member to which the information is distributed but also the extraction condition data including various parameters such as a particular sex, a particular age, and a particular aroma base name, and acquires the data related to the member or the aroma cartridge 14 having those attributes as a response from the messaging server device 11.

In the above embodiment, the fortunetelling information provision server device 15 requests the data related to the user and the aroma cartridge 14 from the messaging server device 11, the additional information (fortunetelling information) is generated in the fortunetelling information provision server device 15, and the generated additional information is directly transmitted from the fortunetelling information provision server device 15 to the terminal device 12. However, the present invention is not limited thereto.

Therefore, for example, the user may request the distribution of the additional information from the messaging server device 11, the messaging server device 11 may acquire the necessary data from the fortunetelling information provision server device 15, and the generated additional information may be distributed from the messaging server device 11 to the terminal device 12.

Further, information exchange in another format may be enabled; for example, the video calling or the exchange of data files may be achieved via the messaging server device 11.

In the above embodiment, the aroma emission instruction data are included explicitly in the message data or the voice calling data transmitted to the terminal device 12 of another member via the messaging server device 11; however, the present invention is not limited thereto. For example, in the case of a configuration in which the aroma is emitted every time the message or calling is received from a predetermined member, the message data or the calling data themselves serve as the aroma emission instruction data.

In the above embodiment, the aroma cartridge 14 includes the memory chip 143 recording the data in the flash memory; however, the means of the aroma cartridge 14 for holding data is not limited to the flash memory and various other methods are applicable. For example, a method in which data are held in a readable and rewritable manner using a magnetic recording means, a method in which data are held in a read-only manner using an optical recording means, a method in which data are held by forming an image such as a bar code on a surface of the aroma cartridge 14, and a method in which data are held by providing unevenness on a surface of the aroma cartridge 14 are given.

In the above embodiment, the user needs to load the aroma cartridge 14 in order to make the message exchange or the voice calling via the messaging server device 11. However, the present invention is not limited thereto. For example, the loading of the aroma cartridge 14 on the message transmission side may be optional, or in the case where the message is transmitted to the terminal device 12 not having the aroma cartridge 14 loaded therein, the loading of the aroma cartridge 14 may be demanded and the aroma may be emitted upon the loading.

In the above embodiment, the amount of releasing the aroma liquid is led from the number of times of releases; however, the amount may be alternatively measured by another unit, such as "0.01 ml" or "0.01 mg".

The above embodiment has not described the source of the aroma liquid to be contained in the aroma cartridge 14. The aroma cartridge 14 may be sold as a package in which the aroma liquid formed by blending particular undiluted liquid is contained in the aroma cartridge 14 by a cartridge selling company, etc. Alternatively, a member may create an original aroma cartridge 14 by blending and pouring the undiluted liquid purchased separately into an empty aroma cartridge 14.

In the latter case, a website where the original aroma cartridges 14 are registered may be created, so that the members register the aroma base names of their original aroma cartridges 14 in the cartridge database (see FIG. 9) and the aroma cartridge 14 can be used in the instant messaging system 1.

The mechanism disclosed in the present invention is not limited to the method in which the messaging among the users is accompanied by aroma emission. For example, the system of the present invention may be used for sharing the aroma in the same space or in spaces apart among a number of users.

For example, when a moving image is reproduced in the terminal device 12 according to the moving image data downloaded via the Internet 19 in a state that the aroma cartridge 14 with the aroma indicated in advance is loaded in the aroma adapter 13, the aroma may be emitted at a predetermined timing according to the content of the moving image in accordance with the aroma emission instruction data included in the moving image data. In this case, the users viewing the same moving image can share the same experience by experiencing the same aroma through the nose while enjoying the same moving image through the eyes and the ears at different times and in different places.

As another example, in the event where many people gather, such as a concert, the participants can share the aroma by spreading the aroma over the event hall. Specifically, an event organizer asks the participants to register in the instant messaging system 1 and bring the terminal device 12 with the aroma emitting adapter 13 connected thereto. On the day of the event, the participants get the aroma cartridge 14 at the entrance of the event hall, for example. The participant sets the distributed aroma cartridge 14 in his/her own aroma emitting adapter 13. The organizer narrows the participants in the messaging app on the basis of the cartridge type ID of the distributed aroma cartridge 14, and transmits the message with the aroma emission instruction to those participants at an appropriate timing based on the progress in the event. In response to the message, the aroma is emitted from the terminal devices 12 of the participants, so that the aroma spreads over the event hall.

If the seats for the participants are fixed in the event hall, for example, the participants can experience different aromas for every area in the event hall by distributing different aroma cartridges 14 for every area. Further, the aroma in the hall can be variously changed by distributing the aroma cartridges 14 so that the different aromas are set at equal intervals in the hall and emitting the different aromas with desirable amounts in accordance with the event scenes.

Instead of distributing the aroma cartridges 14 at the entrance of the event hall, for example, the aroma cartridges 14 may be distributed when the event tickets are sold or the aroma cartridges 14 having the ticket function may be sold instead of the paper ticket, and the organizer may ask the participants to bring the aroma cartridges 14. For allowing the aroma cartridge 14 to function as the ticket, for example, the ticket information (such as the seat number) and a program for displaying the information may be stored in the memory chip 143 of the aroma cartridge 14. The participants display the cartridge information in the terminal device 12 having the aroma cartridge 14 loaded therein and show the information at the entrance of the event hall, so that the entry into the event hall is permitted and the participants can know where to sit.

Instead of distributing the particular aroma cartridges 14 for the event, the participants may freely bring the aroma cartridges 14 loaded in the terminal devices 12, with which the participants can spread the aroma throughout the event. For example, the event organizer narrows the participants based on the positional information and makes groups according to the aroma base names. Then, along with the progress in the event, for example, the organizer orders the terminal devices 12 of the participants having the aroma cartridges 14 with the citrus-base aroma loaded therein to emit the aroma, thereby spreading the citrus-base aroma over the hall; similarly, the floral-base aroma can be spread instead.

In the case where the event is distributed online such as on TV or in the streaming distribution via the Internet 19, the users who enjoy the event on the TV or the terminal devices 12 can experience the same aroma as if they were in the hall. For example, the users who cannot join the event purchase the aroma cartridge 14 recording the predetermined cartridge ID for the event and load the aroma cartridge 14 into the aroma emitting adapter 13 in advance. Then, in accordance with the message with the aroma emission instruction transmitted from the event organizer sequentially, the same aroma as that spread in the hall can be emitted from the terminal device 12. Thus, the users can enjoy the images of the event just as much as the participants in the hall by experiencing the aroma while watching the event on the TV or the terminal devices 12.

In the instant messaging system 1, the access among the users is allowed or restricted based on the various attribute data of the users registered in the user database and the various attribute data of the aroma cartridges 14 loaded by the users registered in the cartridge database in accordance with the message friend judgment condition data or the calling friend judgment condition data of the user database (see FIG. 8) and the access condition data of the cartridge database (see FIG. 9). However, the content and the storage location of the condition data and the kind of the attribute used as the reference for allowing or restricting the access based on the condition data can be variously selected.

For example, the access condition data may be stored not in the cartridge database managed by the messaging server device 11 but in the memory chip 143 of the aroma cartridge 14. In this case, for example, the messaging app may be configured so that the terminal device 12 having accepted the request of the message exchange or the voice call reads out the access condition data stored in the memory chip 143 of the aroma cartridge 14 loaded in the terminal device 12, acquires the attribute data of the user that has transmitted the request or his/her aroma cartridge 14, and judges whether the attribute data acquired from the messaging server device 11 satisfy the access condition data read out from the memory chip 143.

In the above embodiment, "pair ID->message exchange allowed" meaning that the message exchange is allowed only between the users having a pair of aroma cartridges 14 with the serial cartridge ID numbers loaded therein is introduced as the example of the access condition data. Such a pair of aroma cartridges 14 may be formed integrally in a manner that the user having purchased the pair can separate it. The aroma cartridges 14 as a pair are used by a man and a woman of the couple typically, for exchanging the messages. Therefore, the couple having purchased the pair of aroma cartridges 14 at a convenience store or the like separates and shares the aroma cartridges 14, so that they assure their mutual love as a couple.

As another example of the access condition data, a user of the terminal device 12 with the aroma cartridge 14 recording a particular cartridge type ID loaded therein is allowed to exchange the message with a particular user for a predetermined number of times (for example, 10 times). For example, by selling the aroma cartridge 14 in which the access condition data for permitting the message exchange with a popular artist for a predetermined number of times, fans of the artist can purchase the aroma cartridge 14 and enjoy the message exchange accompanied by the aromas with the artist.

Note that the specific numerals, configurations of the screens, data configurations, and procedure of the process, etc. used in the above embodiment are just examples for describing the present invention and the present invention is not limited to those specific content.

INDUSTRIAL APPLICABILITY

The present invention is effective for wide information exchange among individuals, and contributes to service industries such as manufacturers, whole sellers, and retailers by manufacturing and selling a number of aroma emitting adapters and aroma cartridges.

EXPLANATION OF NUMERALS 1 instant messaging system
11 messaging server device
12 terminal device
13 aroma emitting adapter
14 aroma cartridge
15 fortunetelling information provision server device
19 Internet
111 reception unit
112 transmission unit
113 storage unit
114 calculation unit
121 reception unit
122 transmission unit
123 storage unit
124 display unit
125 input unit
126 control unit
131 data input/output terminal
132 hollow part
133 release unit
134 reading unit
135 writing unit
136 remaining amount measurement unit
137 control unit
141 spray hole
142 button
143 memory chip
151 reception unit
152 transmission unit
153 storage unit
154 calculation unit

The invention claimed is:

1. A server device comprising:
reception unit that receives data transmitted from another communication device;
storage unit that stores the data;
calculation unit that performs a calculation process; and
transmission unit that transmits the data to another communication device, wherein:
the reception unit receives from any of a plurality of terminal devices capable of having an aroma cartridge as a cartridge containing aroma liquid loaded therein, terminal identification data for identifying the terminal device and cartridge identification data for identifying the aroma cartridge currently loaded or a type of aroma liquid contained in the aroma cartridge;
the storage unit stores, while associating with the terminal identification data received from one terminal device by the reception unit, the cartridge identification data received from the one terminal device as the entire or a part of attribute data representing an attribute of the one terminal device;
the reception unit receives from any of the plural terminal devices, request data for requesting transmission of status data representing the current loading state of the aroma cartridge in each of one or more terminal devices among the plural terminal devices;
the calculation unit generates, upon the reception of the request data in the reception unit, the status data based on the terminal identification data stored in the storage unit and the attribute data stored while being associated with the terminal identification data in response to the request data; and
the transmission unit transmits the status data generated by the calculation unit to the terminal device that has transmitted the request data.

2. The server device according to claim 1, wherein:
the reception unit receives from any terminal device of the plural terminal devices, message data representing a message or voice calling data representing a calling addressed to a terminal device that is different from the any terminal device of the plural terminal devices; and
the transmission unit transmits the message data or the voice calling data to the terminal device to which the message data or the voice calling data are addressed, upon the reception of the message data or the voice calling data in the reception unit.

3. The server device according to claim 2, wherein:
the storage unit stores judging condition data representing a condition for judging whether exchange of message data representing a message or voice calling data representing a calling among the plural terminal devices is allowed or not based on the terminal identification data stored in the storage unit or the attribute data stored while being associated with the terminal identification data; and
the calculation unit judges the terminal device to which the message data or the voice calling data can be transmitted on the basis of the judging condition data stored in the storage unit, and generates the status data related to the judged terminal device.

4. The server device according to claim 1, wherein:
the reception unit receives from any terminal device of the plural terminal devices, at least one of data on the number of times of releases representing the number of times of releasing the aroma liquid from the aroma cartridge loaded in the terminal device, data on the amount of release representing the amount of aroma liquid released from the aroma cartridge, and data on the remaining amount representing the remaining amount of the aroma liquid contained in the aroma cartridge; and
the storage unit stores at least one of the data on the number of times of releases, the data on the amount of release, and the data on the remaining amount that has been received by the reception means unit, as a part of the attribute data, while associating the data with the terminal identification data for identifying the terminal device that has transmitted the data.

5. The server device according to claim 1, wherein:
the reception unit receives from any terminal device of the plural terminal devices, positional data representing current location of the terminal device;
the storage unit stores the positional data received by the reception unit as a part of the attribute data while associating the positional data with the terminal identification data for identifying the terminal device that has transmitted the positional data; and
the calculation unit generates the status data representing the position of each terminal device on a map on the basis of the positional date included in the attribute data stored in the storage unit.

6. The server device according to claim 1, wherein:
the reception unit receives from a communication device, extraction condition data representing a condition for extracting one or more terminal devices on the basis of the terminal identification data or the attribute data;
the calculation unit extracts the terminal identification data satisfying the condition represented by the extraction condition data received by the reception unit and the attribute data stored while being associated with the terminal identification data, from among the terminal identification data stored in the storage unit and the attribute data stored while being associated with the terminal identification data; and
the transmission unit transmits to the communication device, the terminal identification data and the attribute data stored while being associated with the terminal identification data that have been extracted by the calculation unit.

7. The server device according to claim 1, wherein:
the reception unit receives the extraction condition data representing the condition for extracting one or more terminal devices on the basis of the attribute data from any terminal device of the plural terminal devices; and
the calculation means unit extracts the attribute data satisfying the condition represented by the extraction condition data received by the reception unit from the terminal device from among the attribute data stored in the storage unit, and generates the status data related to the terminal device represented by the terminal identification data stored in the storage unit while being associated with the extracted attribute data.

8. A method comprising:
a step in which a server device receives from any terminal device of a plural terminal devices to which an aroma cartridge containing aroma liquid can be loaded, terminal identification data for identifying the terminal device and cartridge identification data for identifying the aroma cartridge currently loaded or a type of aroma liquid contained in the aroma cartridge;
a step in which the server device stores, while associating with the terminal identification data received from one terminal device by a reception unit, the cartridge identification data received from the one terminal device as the entire or a part of attribute data representing an attribute of the one terminal device;
a step in which the server device receives from any terminal device of the plural terminal devices, request data for requesting transmission of status data representing the current loading state of the aroma cartridge in each of one or more terminal devices among the plural terminal devices;
a step in which the server device generates, upon the reception of the request data, the status data based on the stored terminal identification data and the attribute data stored while being associated with the terminal identification data in response to the request data; and
a step in which the server device transmits the generated status data to the terminal device that has transmitted the request data.

9. The method according to claim 8, further comprising:
a step in which the server device receives from any terminal device of the plural terminal devices, message data representing a message or voice calling data representing a calling addressed to a terminal device that is different from the any terminal device of the plural terminal devices; and
a step in which the server device transmits the message data or the voice calling data to the terminal device to which the message data or the voice calling data are addressed, upon the reception of the message data or the voice calling data.

10. The method according to claim 9, further comprising a step in which the server device stores judging condition data representing a condition for judging whether exchange of message data representing a message or voice calling data representing a calling among the plural terminal devices is allowed or not based on the stored terminal identification data or the attribute data stored while being associated with the terminal identification data,
wherein in the step of generating the status data, the server device judges the terminal device to which the message data or the voice calling data can be transmitted on the basis of the stored judging condition data and generates the status data related to the judged terminal device.

11. The method according to claim 8, further comprising:
a step in which the server device receives from any terminal device of the plural terminal devices, at least one of data on the number of times of releases representing the number of times of releasing the aroma liquid from the aroma cartridge loaded in the terminal device, data on the amount of release representing the amount of aroma liquid released from the aroma cartridge, and data on the remaining amount representing the remaining amount of the aroma liquid contained in the aroma cartridge; and
a step in which the server device stores at least one of the data on the number of times of releases, the data on the amount of release, and the data on the remaining amount that has been received, as a part of the attribute data, while associating the data with the terminal identification data for identifying the terminal device that has transmitted the data.

12. The method according to claim 8, further comprising:
a step in which the server device receives from any terminal device of the plural terminal devices, positional data representing current location of the terminal device; and
a step in which the server device stores the received positional data as a part of the attribute data while associating the positional data with the terminal identification data for identifying the terminal device that has transmitted the positional data, wherein
in the step of generating the status data, the server device generates the status data representing the position of each terminal device on a map on the basis of the positional date included in the stored attribute data.

13. The method according to claim 8, further comprising:
a step in which the server device receives from a communication device, extraction condition data representing a condition for extracting one or more terminal devices on the basis of the terminal identification data or the attribute data;
a step in which the server device extracts the terminal identification data satisfying the condition represented by the received extraction condition data and the attribute data stored while being associated with the terminal identification data, from among the stored terminal identification data and the attribute data stored while being associated with the terminal identification data; and
a step in which the server device transmits to the communication device, the terminal identification data and the attribute data stored while being associated with the terminal identification data that have been extracted.

14. The method according to claim 8, further comprising a step in which the server device receives the extraction condition data representing the condition for extracting one or more terminal devices on the basis of the attribute data from any terminal device of the plural terminal devices, wherein
in the step of generating the status data, the server device extracts the attribute data satisfying the condition represented by the extraction condition data received from the terminal device from among the stored attribute data, and generates the status data related to the terminal device represented by the terminal identification data stored while being associated with the extracted attribute data.

15. A non-transitory computer-readable medium storing a program having computer-executable instructions allowing a computer having a communication unit that performs data communication with another communication device to function as the reception unit, the storage unit, the calculation unit, and the transmission unit included in the server device according to claim 1.

16. A terminal device comprising:
reception unit that receives data transmitted from another communication device;
storage unit that stores the data;
transmission unit that transmits the data to another communication device;
display unit that displays an image;
input unit that accepts data input from a user by generating predetermined data in response to predetermined user operation;
aroma generating adapter that generates aroma; and
control unit that controls another configuration part, wherein:
the aroma generating adapter includes a hollow part that accepts loading of an aroma cartridge containing aroma liquid, release unit that releases a part of the aroma liquid contained in the aroma cartridge loaded in the hollow part, and reading unit that reads data recorded in the aroma cartridge loaded in the hollow part;
the transmission unit transmits to a server device, terminal identification data for identifying the own device stored in the storage unit or terminal identification data for identifying the own device generated by the input unit in response to user operation;
the reading unit reads the data recorded in the aroma cartridge currently loaded in the hollow part;
the transmission unit transmits to the server device, cartridge identification data for identifying the aroma cartridge or a type of the aroma liquid included in the data read by the reading unit;
the transmission unit transmits to the server device, request data for requesting transmission of status data representing the current loading state of the aroma cartridge in each of one or more terminal devices among the plural terminal devices except the own device;
the reception unit receives the status data transmitted from the server device as a response to the request data transmitted by the transmission unit; and
the display unit displays an image representing content of the status data received by the reception unit.

17. The terminal device according to claim 16, wherein:
the reception unit receives from the server device, message data representing a message or voice calling data representing a calling from a terminal device that is different from the own terminal device; and
the control unit causes the release unit to release the aroma liquid upon the reception of the message data or the voice calling data in the reception unit.

18. The terminal device according to claim 16, wherein:
the transmission unit transmits to the server device, at least one of data on the number of times of releases representing the number of times of releasing the aroma liquid from the aroma cartridge loaded in the hollow part, data on the amount of release representing the amount of aroma liquid released from the aroma cartridge, and data on the remaining amount representing the remaining amount of the aroma liquid contained in the aroma cartridge.

19. The terminal device according to claim 16, further comprising positional data acquiring unit that acquires positional data representing a current position of the own device, wherein
the transmission unit transmits the positional data acquired by the positional data acquiring unit to the server device.

20. The terminal device according to claim 16, wherein:
the input unit generates extraction condition data representing a condition for extracting one or more terminal devices on the basis of attribute data representing an attribute of the terminal device in response to user operation;
the transmission unit transmits the extraction condition data generated by the input unit to the server device; and
the reception unit receives the status data related to the terminal device extracted in the server device on the basis of the extraction condition data transmitted from the transmission unit.

21. A method comprising:
a step in which a terminal device including aroma generating adapter for generating aroma transmits to a server device, terminal identification data for identifying the stored own device or terminal identification data for identifying the own device generated in response to user operation;

a step in which the terminal device reads data recorded in an aroma cartridge containing aroma liquid loaded in the aroma generating adapter;

a step in which the terminal device transmits to the server device, cartridge identification data for identifying the aroma cartridge or a type of the aroma liquid included in the read data;

a step in which the terminal device transmits to the server device, request data for requesting transmission of status data representing a current loading state of the aroma cartridge in each of one or more terminal devices of plural terminal devices except the own device;

a step in which the terminal device receives the status data transmitted from the server device as a response to the transmitted request data; and a step in which the terminal device displays an image representing content of the received status data.

22. The method according to claim 21, further comprising:

a step in which the terminal device receives from the server device, message data representing a message or voice calling data representing a calling transmitted from one terminal device of the plural terminal devices except the own device; and a step in which the terminal device causes the aroma generating adapter to release the aroma liquid from the aroma cartridge loaded in the aroma generating adapter upon the reception of the message data or the voice calling data.

23. The method according to claim 21, further comprising a step in which the terminal device transmits to the server device, at least one of data on the number of times of releases representing the number of times of releasing the aroma liquid from the aroma cartridge loaded in the aroma generating adapter, data on the amount of release representing the amount of aroma liquid released from the aroma cartridge, and data on the remaining amount representing the remaining amount of the aroma liquid contained in the aroma cartridge.

24. The method according to claim 21, further comprising:

a step in which the terminal device acquires positional data representing a current position of the own device; and a step in which the terminal device transmits the acquired positional data to the server device.

25. The method according to claim 21, further comprising:

a step in which the terminal device generates extraction condition data representing a condition for extracting one or more terminal devices on the basis of attribute data representing an attribute of the terminal device in response to user operation; and a step in which the terminal device transmits the generated extraction condition data to the server device, wherein in the step of receiving the status data, the terminal device receives the status data related to the terminal device extracted in the server device on the basis of the transmitted extraction condition data.

26. A non-transitory computer-readable medium storing a program having computer-executable instructions allowing a computer having a communication unit that performs data communication with another communication device and aroma generating adapter that generates aroma to function as the reception unit, the storage unit, the transmission unit, the display unit, the input unit, and the control unit included in the terminal device according to claim 16.

* * * * *